(12) United States Patent
Alam et al.

(10) Patent No.: US 9,539,140 B2
(45) Date of Patent: Jan. 10, 2017

(54) EYE DROPPER POSITIONING AND GUIDING APPARATUS

(71) Applicant: KING SAUD UNIVERSITY, Riyadh (SA)

(72) Inventors: Mohd Aftab Alam, Riyadh (SA); Fahad Ibrahim Al-Jenoobi, Riyadh (SA); Abdullah M. Al-Mohizea, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 87 days.

(21) Appl. No.: 14/571,622

(22) Filed: Dec. 16, 2014

(65) Prior Publication Data
US 2016/0089266 A1    Mar. 31, 2016

Related U.S. Application Data

(62) Division of application No. 14/497,279, filed on Sep. 25, 2014, now Pat. No. 9,072,581.

(51) Int. Cl.
*A61F 9/00* (2006.01)
*A61M 11/00* (2006.01)
(Continued)

(52) U.S. Cl.
CPC ........... *A61F 9/0026* (2013.01); *A61F 9/0008* (2013.01); *A61M 11/00* (2013.01); *A61M 11/006* (2014.02);
(Continued)

(58) Field of Classification Search
CPC ................ A61F 2230/0091; A61F 2250/0004; A61F 9/0008; A61F 9/0026; A61H 35/02; A61M 11/00; A61M 11/006; A61M 11/007; A61M 11/008; A61M 2210/0612; A61M 35/00; A61M 35/003; B65D 47/18; B65D 47/185; B65D 83/30; F16F 1/027; F16F 2234/06; F16F 2238/022
See application file for complete search history.

(56) References Cited

U.S. PATENT DOCUMENTS 2,676,592 A    4/1954 Wood
2,398,911 A    8/1959 Taylor
(Continued)

OTHER PUBLICATIONS

"Ableware Auto Drop Eye Drop Guide," http://www.quill.com/other-daily-living-aids/cbs/446486.html?cm_mmc=SEM_PLA_CB_446486 (Last Accessed on Apr. 11, 2014)p. 1.

*Primary Examiner* — Adam Marcetich
(74) *Attorney, Agent, or Firm* — Richard C. Litman

(57) ABSTRACT

The eye dropper positioning and guiding apparatus includes a resilient guiding device having a selectively compressible member having a first opening adapted to receive an eye drop applicator and a second opening adapted to position an eye within an area of the second opening to receive a fluid from the eye drop applicator. The selectively compressible member is adapted for selective linear and nonlinear movement in relation to the eye positioned within the area of the second opening. The eye dropper positioning and guiding apparatus can also include a support base and a resilient guiding device including a selectively expandable member having a plurality of concentric loops having an outermost loop and an innermost loop, adapted for selective linear and nonlinear movement, or a support base and a resilient guiding device including a plurality of concentric, interconnected rings adapted for selective linear and nonlinear movement in relation to an eye.

5 Claims, 15 Drawing Sheets

(51) Int. Cl.
*A61M 35/00* (2006.01)
*B65D 47/18* (2006.01)
*B65D 83/30* (2006.01)
*A61H 35/02* (2006.01)
*F16F 1/02* (2006.01)

(52) U.S. Cl.
CPC ............ *A61M 11/008* (2014.02); *A61M 35/00* (2013.01); *A61M 35/003* (2013.01); *B65D 47/18* (2013.01); *A61F 2230/0091* (2013.01); *A61F 2250/0004* (2013.01); *A61H 35/02* (2013.01); *A61M 11/007* (2014.02); *A61M 2210/0612* (2013.01); *B65D 47/185* (2013.01); *B65D 83/30* (2013.01); *F16F 1/027* (2013.01); *F16F 2234/06* (2013.01); *F16F 2238/022* (2013.01)

(56) References Cited

U.S. PATENT DOCUMENTS

| | | | |
|---|---|---|---|
| 3,058,466 A | 10/1962 | Routsong | |
| 3,779,245 A | 12/1973 | Windsor | |
| 3,913,575 A | 10/1975 | Windsor | |
| 3,934,590 A | 1/1976 | Campagna et al. | |
| 4,134,403 A | 1/1979 | Johnsen et al. | |
| 4,183,355 A | 1/1980 | Meckler | |
| 4,344,430 A | 8/1982 | Astrove | |
| 4,493,119 A * | 1/1985 | Baumann | A61H 35/02 239/590.3 |
| 4,531,944 A | 7/1985 | Bechtle | |
| 4,685,906 A | 8/1987 | Murphy | |
| 4,834,727 A | 5/1989 | Cope | |
| 4,960,407 A | 10/1990 | Cope | |
| 4,973,322 A | 11/1990 | Jewart | |
| 4,981,479 A | 1/1991 | Py | |
| 5,007,905 A | 4/1991 | Bauer | |
| 5,037,406 A * | 8/1991 | Smith | A61F 9/0026 222/568 |
| 5,059,188 A | 10/1991 | Goddard | |
| 5,064,420 A * | 11/1991 | Clarke | A61F 9/0026 604/295 |
| 5,201,726 A * | 4/1993 | Kirkham | A61H 35/02 222/318 |
| 5,578,020 A | 11/1996 | Mosley | |
| 5,810,794 A | 9/1998 | Peplinski | |
| 5,976,116 A | 11/1999 | Muroff | |
| 6,090,086 A | 7/2000 | Bolden | |
| 6,325,784 B1 | 12/2001 | Muroff | |
| 6,398,051 B1 * | 6/2002 | Brozell | B65D 51/26 206/540 |
| 6,530,908 B1 | 3/2003 | Sherman et al. | |
| 6,736,802 B1 | 5/2004 | Recanati | |
| D499,804 S | 12/2004 | Sherman | |
| 7,309,329 B2 | 12/2007 | Cress | |
| 7,784,936 B2 | 8/2010 | Stinson | |
| D672,870 S | 12/2012 | Bertelsen | |
| 8,348,912 B2 | 1/2013 | Rehkemper et al. | |
| 8,486,031 B2 | 7/2013 | Bogdan | |
| D694,403 S | 11/2013 | Lensch | |
| 8,672,904 B1 * | 3/2014 | Schultz | A61H 35/02 222/386 |
| 2002/0073934 A1 * | 6/2002 | Barney | A61D 7/00 119/831 |
| 2002/0164921 A1 * | 11/2002 | Wilkinson | A63H 11/06 446/308 |
| 2003/0135170 A1 | 7/2003 | Kapple | |
| 2004/0267214 A1 | 12/2004 | Kerssies | |
| 2009/0259204 A1 | 10/2009 | Galdeti et al. | |
| 2010/0286633 A1 * | 11/2010 | Marx | A61F 9/0026 604/296 |
| 2010/0286634 A1 * | 11/2010 | Marx | A61F 9/0026 604/302 |
| 2011/0118678 A1 | 5/2011 | Rehkemper et al. | |
| 2012/0150132 A1 | 6/2012 | Cress | |
| 2012/0214650 A1 * | 8/2012 | Jahns | A63B 21/0004 482/111 |
| 2014/0316360 A1 * | 10/2014 | Ekfeldt | A61F 5/445 604/344 |

* cited by examiner

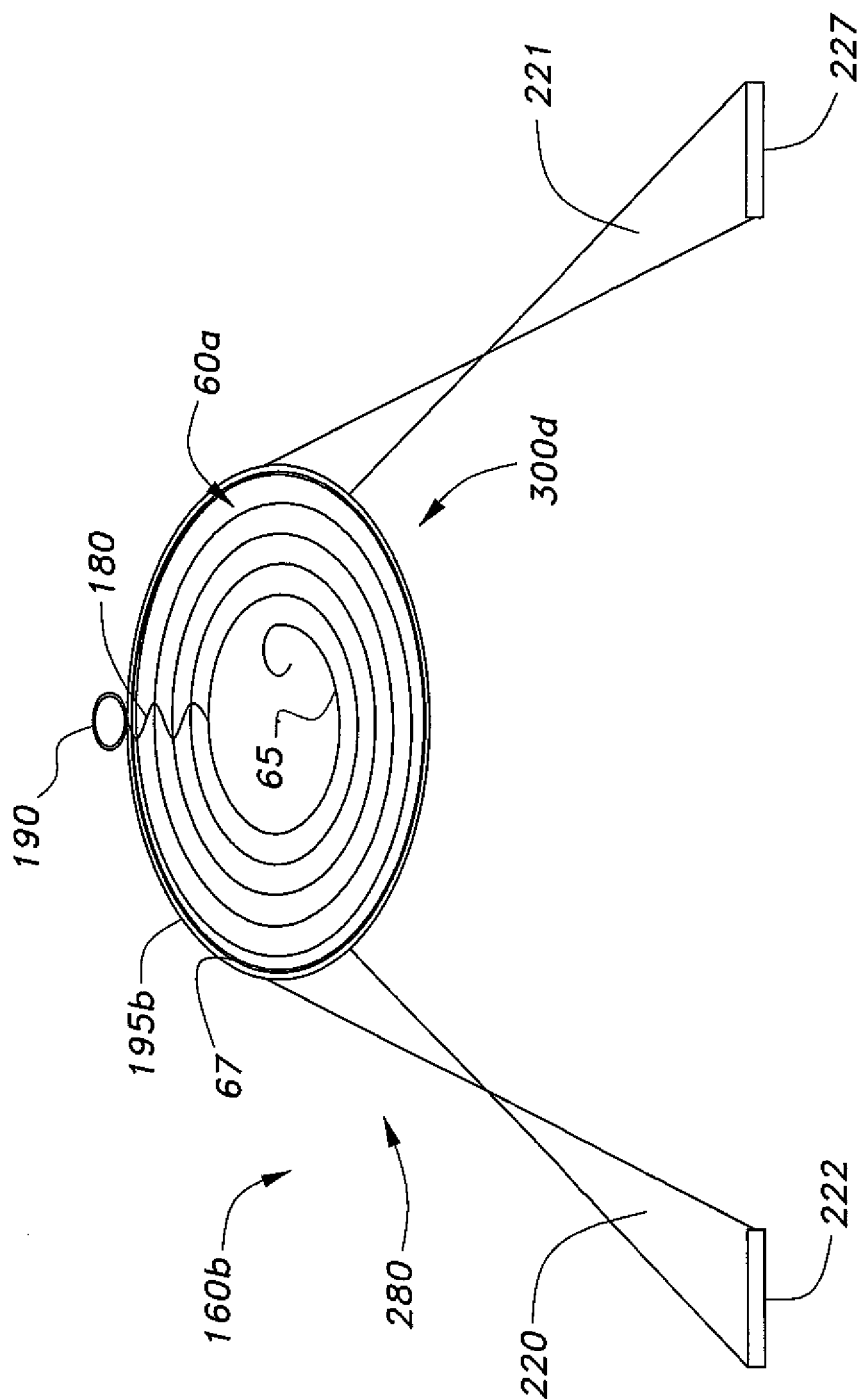

EYE DROPPER POSITIONING AND GUIDING APPARATUS

CROSS REFERENCE TO RELATED APPLICATIONS

This is a divisional of our prior application Ser. No. 14/497,279, filed Sep. 25, 2014, now pending.

BACKGROUND OF THE INVENTION

1. Field of the Invention

The present invention relates to an apparatus to position and guide an eye drop applicator to improve the accuracy when administering eye drops into an eye. More specifically, the present invention allows for one or more of selective linear and nonlinear movement to selectively adjust a height and a position of an eye drop applicator in relation to an eye, such as including one or more of vertical, lateral, oblique, and various combinations, paths and directions of movement of the eye drop applicator, to aid in the administration of an eye drop into an eye and to aid in protecting the eye from contact with the nozzle of the eye drop applicator.

2. Description of the Related Art

Many people use eye drops as treatment for microbial infections, glaucoma, dry eye syndrome, and irritation resulting from dust and other small foreign objects. People who use contact lenses for long periods of time also tend to use eye drops to re-wet their eyes. For effective treatment, the eye drops can be administered regularly at one or more times during the day, such as about three to four times a day or as prescribed by an ophthalmologist, for example. Eye drops are typically packaged in a resilient eye drop applicator bottle having a nozzle through which eye drop(s) is/are administered into the eye.

Self-administration, for example, of eye drops using known eye drop applicators, however, can be challenging and can lead to injury for various reasons. It can be difficult to properly position or align the eye drop applicator to administer eye drops at a particular location in relation to the eye while tilting the head back and simultaneously administering the eye drops. This can result in inadvertently wasting medicine or, even worse, an inability to administer the correct dosage to the eye. Also, since the eye lids and eye lashes are typically sensitive and can be subject to a reflex action when a foreign object approaches the eye, the eye lids can sometimes prevent at least a portion of the eye drops from entering the eye. Further, the close positioning of a nozzle of an eye drop applicator in front of the eye can lead to missed judgment in the eye drop application, since objects relatively close to the eye can become blurred, and can thereby cause the nozzle of the eye drop applicator to come in contact with the corneal region of the eye as can potentially cause or increase the likelihood of infection, irritation or injury to the eye. Also, such potential difficulties in eye drop administration can be more likely in individuals that experience reduced vision related to various eye conditions or coordination difficulties, such as hand tremors, as can hinder the ability to correctly position or aim the eye drop applicator, for example.

Various apparatuses for eye drop applicators that attempt to remedy the problems related to the self-administration of eye-drops are known. However, many of these known apparatuses for eye drop applicators can be selective in their application, as well as typically not being adapted to work with eye drop applicators having nozzles of a non-uniform design, size, or shape or nozzles of varying lengths, for example. Therefore, such known apparatuses for eye drop applicators, when used for other than their intended selective application, can likely increase the likelihood that the nozzles that dispense the eye drops can come in contact with the corneal region of the eye, as can increase the possibility of damage to the eye. Further, such known apparatuses for eye drop applicators can be difficult to adapt to work with individuals having different facial features (e.g. inter-pupillary distance and, the width and height of the nose) or individuals having bulging eyes or eyes below a relatively normal position because of possible difficulty or inability in achieving an acceptable position of an eye drop apparatus in relation to an eye prior to dispensing the medication. Further, by not having a significant ability to allow for or provide an acceptable position of the eye drop applicator, various known apparatuses for eye drop applicators typically can have a reduced suitability for operated, injured, or inflamed eyes, since use of such known apparatuses can likely increase a possibility of the nozzle of the eye drop applicator coming into direct contact with the eye. A likely result of such inadequacies and short comings of known apparatuses for eye drop applicators is that a relatively large majority of eye drops are generally applied or administered without using any positioning or guiding apparatus to position the eye drop applicator relative to the eye or other facial location.

Thus, an eye dropper positioning and guiding apparatus addressing the aforementioned problems is desired.

SUMMARY OF THE INVENTION

Embodiments of an eye dropper positioning and guiding apparatus have a resilient guiding device including a selectively compressible member having a first opening adapted to receive an eye drop applicator and a second opening adapted to position an eye within an area of the second opening to receive a fluid from the eye drop applicator, wherein the selectively compressible member is adapted for one or more of selective linear and nonlinear movement to selectively adjust a height and a position of an eye drop applicator, such as including one or more of vertical, lateral, oblique, and various combinations, paths and directions of movement, in relation to the eye positioned within the area of the second opening to selectively movably position the eye drop applicator in a position in relation to the eye to dispense a fluid from the eye drop applicator into a corresponding portion of the eye.

A further embodiment includes a supporting base being adapted to position over at least a portion of an area of a face proximate to the eye and a resilient guiding device adapted for one or more of selective linear and nonlinear movement to selectively adjust a height and a position of an eye drop applicator, such as including one or more of vertical, lateral, oblique, and various combinations, paths, and directions of movement, in relation to an eye including a spring member having a plurality of concentric loops including an outermost loop and an innermost loop, the innermost loop adapted to receive an eye drop applicator.

Another embodiment includes a supporting base being adapted to position over at least a portion of an area of a face proximate to the eye and also includes a resilient guiding device having concentric, interconnected rings adapted for one or more of selective linear and nonlinear movement to selectively adjust a height and a position of an eye drop applicator, such as including one or more of vertical, lateral, oblique, and various combinations, paths, and directions of movement, in relation to an eye including an innermost ring adapted to receive an eye drop applicator and an outermost ring.

Embodiments of a resilient guiding device can also include at least one safety lock associated with a corresponding at least one connecting member formed from a material selected from the group consisting of a metallic wire type material, a metallic chain type material, a thread type material, or a combination thereof, adapted to connect to an innermost loop or an innermost ring of the resilient guiding device so as to prevent or limit over stretching of the resilient guiding device and protect the eyes. The resilient guiding device can allow for one or more of selective linear and nonlinear movement to selectively adjust a height and a position of an eye drop applicator, such as including one or more of vertical, lateral, oblique, and various combinations, paths, and directions of movement, in relation to the eye, such as when guided by the fingers, for example.

Embodiments of a supporting base can also include a first ring member, with the resilient guiding device being positioned in conjunction with, such as being set on or coupled to, the first ring member, a second ring member adapted to position over a periorbital region of the eye or in proximity to the eye socket, and a plurality of connecting members connecting the first ring member and the second ring member. In other embodiments, the supporting base can include an eye bridge having a holder which can be positioned over the eye, and still other embodiments can include a generally saddle type shape, which can be placed over the nose, so as to support the resilient guiding device, for example.

Further, in other embodiments, the supporting base can include a ring member that can also form a portion of the resilient guiding device or the resilient guiding device can be coupled by at least one resilient member to the ring member. In such embodiments, once the resilient guiding device is coupled to the supporting base, the supporting base including the resilient guiding device can be positioned over the eye or in proximity to the eye socket of the eye. The nozzle of the eye drop applicator can then be inserted through the resilient guiding device and selectively adjusted one or more of linearly and nonlinearly to selectively adjust a height and a position of an eye drop applicator, such selective adjustment including one or more of vertical, lateral, oblique, and various combinations, paths, and directions of movement, towards or away from the eye so as accurately dispense the medication into the eye.

These and other features of the present invention will become readily apparent upon further review of the following specification and drawings.

BRIEF DESCRIPTION OF THE DRAWINGS

FIG. 3D is an elevated perspective view of an embodiment of an eye dropper positioning and guiding apparatus adapted to work with a supporting base including an eye bridge according to the present invention.

Unless otherwise indicated, similar reference characters denote corresponding features consistently throughout the attached drawings.

DETAILED DESCRIPTION OF THE PREFERRED EMBODIMENTS

Figure 1A:
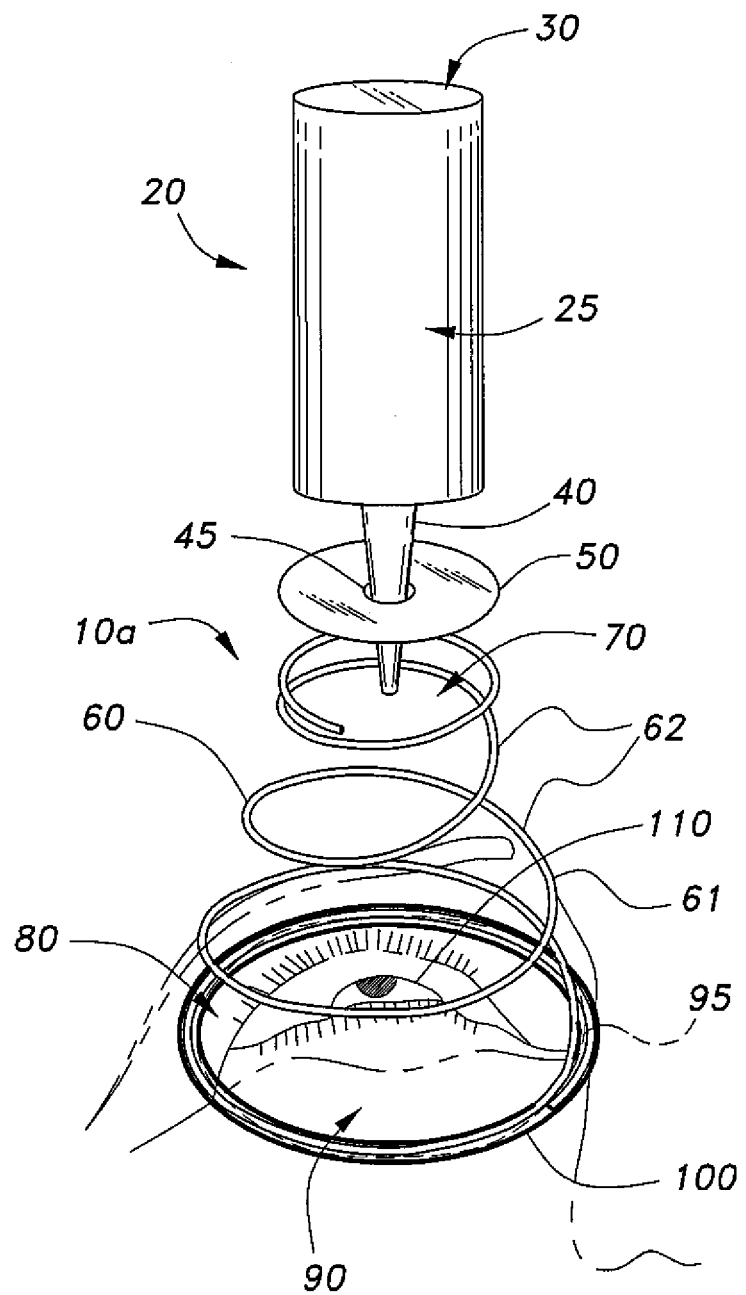
FIG. 1A is an environmental, perspective view of an embodiment of an eye dropper positioning and guiding apparatus being adapted to work with an eye drop applicator having a nozzle according to the present invention.
Figure 1B:
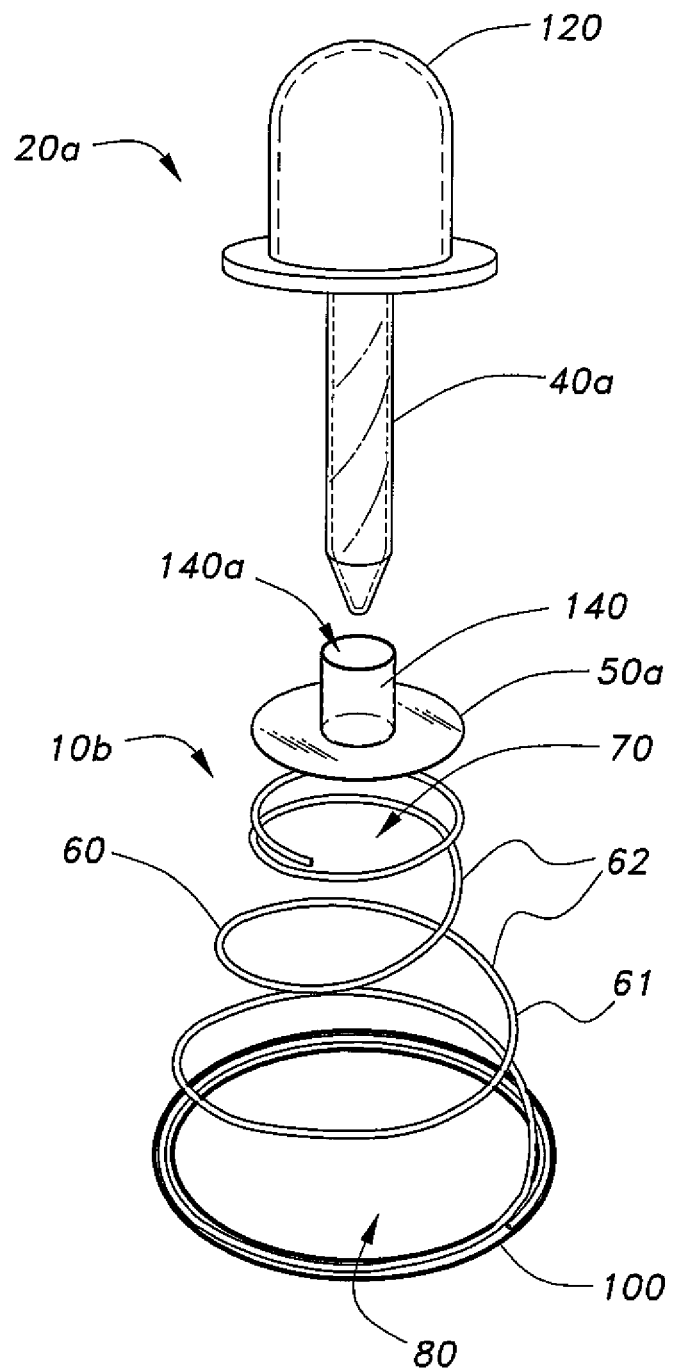
FIG. 1B is an elevated perspective view of an embodiment of an eye dropper positioning and guiding apparatus adapted to work with an eye drop applicator having a barrel and a rubber type bulb according to the present invention.

Referring to FIGS. 1A and 1B, the eye dropper positioning and guiding apparatuses 10a and 10b include a resilient guiding device 60 including a selectively compressible member 61 having a first opening 70 having a first diameter or a first crosswise dimension adapted to receive an eye drop applicator, such as eye drop applicators 20 and 20a, and a second opening 80 of a second diameter or a second crosswise dimension adapted to position an eye 110 within an area of the second opening 80 to receive a fluid from the eye drop applicator, such as eye drop applicators 20 and 20a. The fluid or eye drop(s) dispensed by the eye drop applicator, can include not only a liquid medication but also a cream/gel type or a salve type medication, as well, for example, and should not be construed in a limiting sense. During use, when the person administering the eye medication selectively moves a base 30 or a bulb 120 of an eye drop applicator, such as including one or more of vertical, lateral, oblique, and various combinations, paths and directions of movement, when positioned in the selectively compressible member 61, there is provided one or more of a selective linear and nonlinear direction or path of movement for the eye drop applicator to selectively adjust a height and a position of the eye drop applicator, such as eye drop applicators 20 and 20a, having a nozzle, such as nozzles 40 and 40a, to adjust a position of the nozzle in relation to the eye 110. The selectively compressible member 61 of the resilient guiding device 60 can allow for its one or more of selective linear and nonlinear movement to selectively adjust a height and a position of an eye drop applicator, when positioned therein, in relation to the eye 110, such as including one or more of vertical, lateral, oblique, and various combinations, paths and directions of movement, and that of the nozzle, such as nozzles 40 and 40a, of the eye drop applicator, such as eye drop applicators 20 and 20a, so as to properly align the nozzle with the eye 110 positioned within the area of the second opening 80 to selectively administer a fluid from the eye drop applicator into a corresponding portion of the eye 110. It is to be appreciated that the resilient guiding device 60 including the selectively compressible member 61 can be formed from material that is compressible, flexible, and resilient in nature, such as polymeric or metallic compressible springs, for example.

Figure 3A:
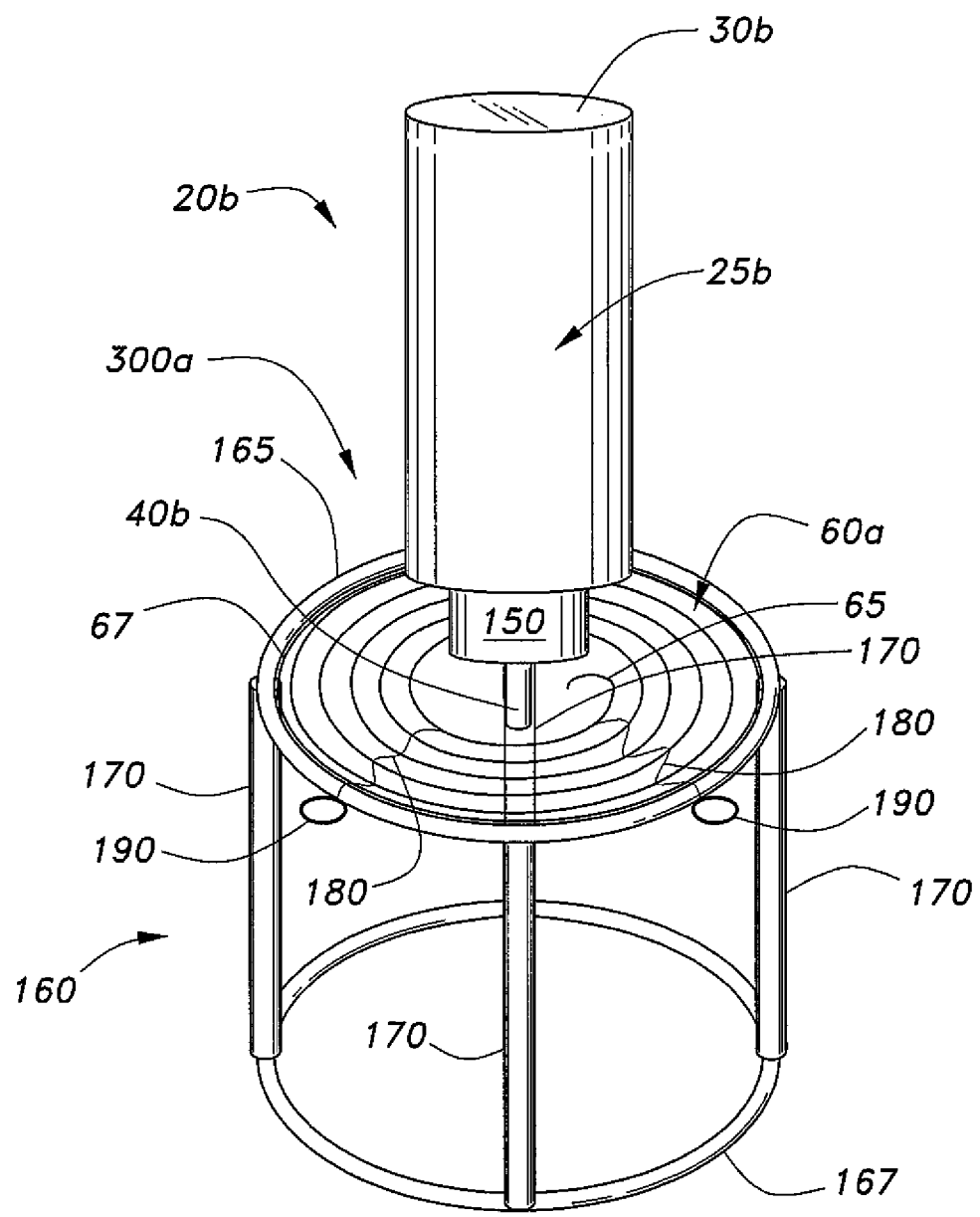
FIG. 3A is an elevated perspective view of an embodiment of an eye dropper positioning and guiding apparatus according to the present invention illustrating a resilient guiding device in a normal state adapted to work with an eye drop applicator.
Figure 3B:
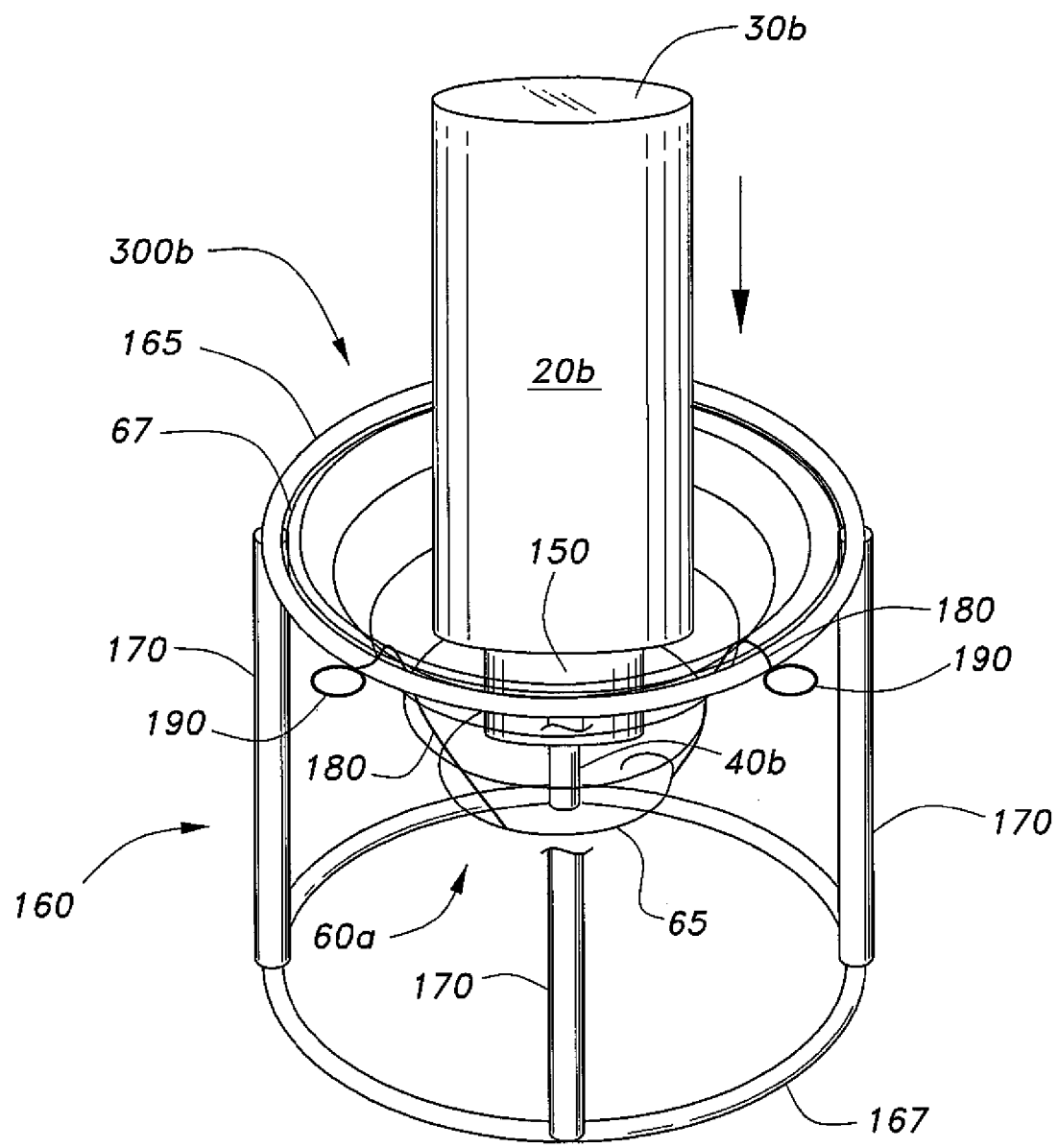
FIG. 3B is an elevated perspective view of an embodiment of an eye dropper positioning and guiding apparatus according to the present invention illustrating an expanded resilient guiding device adapted to work with an eye drop applicator.

Referring to FIGS. 1A and 3A, an eye drop applicator, such as eye drop applicators 20 and 20b, can be used to dispense medicated and non-medicated eye solutions into the eye 110. An eye drop applicator, such as eye drop applicators 20 and 20b, respectively includes a resilient body 25, 25b having a base 30, 30b being in communication with a nozzle, such as nozzles 40 and 40b. The nozzle, such as nozzles 40 and 40b, can be a hollow cylindrical pipe, as can have a tapered configuration, having an opening at both ends, for example. The nozzle, such as the nozzle 40 or the nozzle 40b, can be directly connected to the resilient body 25, as illustrated in FIG. 1A, or the nozzle 40b can be connected to the resilient body 25b via a neck 150, as illustrated in FIGS. 3A, 3B, and 3E. A radial flange can also be provided in between the nozzle, such as nozzles 40 and 40b, and the neck 150. It is to be noted that the nozzle, such as nozzles 40 and 40b, can also be surrounded by a fence-like crown.

By way of operation, the eye drop applicator, such as eye drop applicators 20, 20a and 20b, dispense the eye drop solution through the nozzle, such as nozzles 40, 40a and 40b, after the resilient body 25, 25b or the bulb 120 has been compressed. It is to be noted that an eye drop applicator, such as eye drop applicator 20a, that includes the bulb 120, such as a rubber type bulb and a nozzle, such as nozzle 40a, can have a barrel shape, as illustrated in FIG. 1B, wherein the rubber type bulb 120 can also be used to extract the medication from a container and administer it into the eye 110, for example.

Continuing with reference to FIGS. 1A and 1B, embodiments of the resilient guiding device 60 include a selectively compressible member 61, such as a spiral type spring having a plurality of helical shaped loops 62, wherein one of the plurality of helical shaped loops 62 forms the first opening 70 and another of the plurality of helical shaped loops 62 forms the second opening 80. The first opening 70, being adapted to receive an eye drop applicator, such as eye drop applicator 20, 20a and 20b, and the second opening 80 are on opposite sides of the resilient guiding device 60. Although the resilient guiding device 60 can be of any suitable shape, such as a generally hourglass shape or a generally barrel shape, for example, it is desirable that the resilient guiding device 60 have a conical or a generally conical shape, such as illustrated in FIGS. 1A and 1B, for example. It is to be known that the helical shaped loops 62 are not limited to having a generally circular configuration, but can also include loops having various shapes such as generally rectangular, square, triangular, diamond or elliptical configurations or loops, for example, and should not be construed in a limiting sense. It is to be noted that the second opening 80 can be associated with a supporting base 100, and the resilient guiding device 60 can be positioned in conjunction with, such as being set on or coupled to, the supporting base 100, as being positioned in conjunction with the selectively compressible member 61 formed by the helical shaped loops 62. Also, the supporting base 100 is adapted to fit or be positioned over a periorbital region 90 of the eye 110 or positioned in proximity to an eye socket 95. It is to be noted that the number of consecutive helical shaped loops 62 including the first opening 70 and the second opening 80 of the resilient guiding device 60 typically can vary between three and ten helical loops 62, as can depend on the use or application, and should not be construed in a limiting sense. However, it is desirable that the resilient guiding device 60 have between five and six helical loops 62 including the first opening 70 and the second opening 80, for example.

The gaps between consecutive helical loops 62 of the resilient guiding device 60 provide compressible space so that the resilient guiding device 60 can be compressed and the nozzle, such as nozzles 40, 40a and 40b, of the eye drop applicator, such as eye drop applicator 20, 20a, and 20b, can be selectively adjusted one or more of linearly and nonlinearly to selectively adjust a height and a position of an eye drop applicator, as described herein, in relation to and over the eye 110. Such selective linear and nonlinear adjustment can assist in accurately administering the eye drops into the eye 110 and can prevent or limit the nozzle, such as nozzles 40, 40a, and 40b, of the eye drop applicator, such as applicator 20, 20a and 20b, from coming in contact with the corneal region of the eye 110. For example, if the eye 110 is located below its normal position, the resilient guiding device 60 can be compressed so as to properly apply the eye drops to the eye 110. If, on the other hand, the eye 110, protrudes out from its normal location, the compressive and resilient nature of the resilient guiding device 60 can assist in preventing the nozzle, such as nozzles 40, 40a and 40b, of the eye drop applicator, such as eye drop applicators 20, 20a, and 20b, from coming in contact with the corneal region of the eye 110. The resilient guiding device 60 can allow for one or more of selective linear and nonlinear adjustment to selectively adjust a height and a position of an eye drop applicator in relation to the eye 110, such as including one or more of vertical, lateral, oblique, and various combinations, paths, and directions of movement, prior to and during administration of the liquid eye drop(s) medication. Thus, such selective linear and nonlinear adjustment allowed by the resilient guiding device 60 can aid in the administration of the eye drop(s) liquid.

Since the eye drops can be applied using a variety of eye drop applicators, such as eye drop applicators 20, 20a and 20b, the resilient guiding device 60 can include an attachment member, such as attachment members 50 and 50a, illustrated in FIGS. 1A and 1B, positioned in conjunction with, such as being set on or coupled to, at least one helical loop 62 forming the first opening 70 of the resilient guiding device 60, wherein the attachment member has a third opening, such as a third opening 45 of attachment member 50 and a third opening 140a of a sleeve 140 of the attachment member 50a, of a third diameter or a third crosswise dimension less than the first diameter or the first crosswise dimension of the first opening 70. The attachment members 50 and 50a can be adapted to maintain the nozzle, such as nozzles 40 and 40a of the eye drop applicator, such as eye drop applicators 20 and 20a, in spaced relation to the eye 110, for example.

Also, for example, as illustrated in FIG. 1A, eye drop applicator 20 with nozzle 40 can be supported with an attachment member, such as the attachment member 50, having the inner opening 45 that fits the nozzle 40 of the eye drop applicator 20. By way of operation, the attachment member 50 can be placed in conjunction with at least one helical loop 62 forming the first opening 70 of the resilient guiding device 60 and then the nozzle 40 of the eye drop applicator 20 is passed through the inner opening 45 of the attachment member 50. Further, as illustrated in FIG. 1B, if the eye drop applicator, such as eye drop applicator 20a, includes the bulb 120, such as a rubber type bulb, for example, in communication with a nozzle, such as having a generally barrel shape as can have a generally conical shaped end, such as nozzle 40a, the nozzle 40a can be inserted through the opening 140a of a passage way of the sleeve 140 of the attachment member 50a adapted to fit the nozzle 40a of the eye drop applicator, such as eye drop applicator 20a. Additionally, the attachment members, such as attachment members 50 and 50a, can also prevent or limit nozzles having different shapes and sizes from coming in contact with the corneal region of the eye 110.

By way of operation, the first opening 70 is adapted to receive the nozzle, such as nozzles 40, 40a and 40b, of the eye drop applicator, such as eye drop applicators 20, 20a and 20b, in an inverted position, such as in a position with the nozzle of the eye drop applicator pointing in a downward direction, for example. If, however, the eye drop applicator includes an unconventional or specialized type nozzle, the first opening 70 can receive an attachment member, such as the attachment members 50 and 50a, to receive the nozzle of the eye drop applicator, such as one of eye drop applicators 20 and 20a, in an inverted position. The eye drop applicator, such as one of eye drop applicators 20, 20a, and 20b, is inserted into the first opening 70 formed by a helical shaped loop 62 or into the attachment member, such as attachment members 50 and 50a, if necessary, associated with the first opening 70. At least one helical loop 62 forming the second opening 80 of the resilient guiding device 60 is placed in conjunction with the supporting base 100, or the resilient guiding device 60 can previously have been positioned in conjunction with, such as by being set on or coupled to, the supporting base 100, for example. The head of the person receiving the eye medication is then reclined backwards and the supporting base 100 of the resilient guiding device 60 having the eye drop applicator, such as eye drop applicators 20, 20a and 20b, is placed on the periorbital region 90 of the eye 110 or positioned in proximity to the eye socket 95.

For example, the supporting base 100 of the resilient guiding device 60 can be positioned over the upper eye lid and below the lower eye lid to assist in keeping the eye lids from preventing or limiting the eye drop fluid from reaching the eye 110. Once the supporting base 100 associated with the second opening 80 of the resilient guiding device 60 is placed over the periorbital region 90 of the eye 110 or positioned in proximity to the eye socket 95, the eye drop applicator, such as eye drop applicators 20, 20a and 20b, can be selectively pushed or adjusted downward, such as in a downward vertical or oblique direction, toward the eye 110 and/or can be one or more of selectively linearly and nonlinearly adjusted to selectively adjust a height and a position of an eye drop applicator, as described herein, so that the eye drop(s) fluid can be administered into the eye 110. After the eye drop(s) fluid has/have been administered into the eye 110 and the generally downward directional pressure is removed from the eye drop applicator, such as eye drop applicators 20, 20a, and 20b, the resilient guiding device 60 and the eye drop applicator therein can then return to an original position, such as due to the resilience of guiding device 60, for example, and the eye drop applicator, such as one of eye drop applicators 20, 20a and 20b, can be removed from the resilient guiding device 60.

Referring to FIGS. 1A, 1B, 2A through 2C and 3A through 3K, various exemplary embodiments of eye dropper positioning and guiding apparatuses including various components thereof, such as eye dropper positioning and guiding apparatuses 300a-300k, are illustrated and can include a resilient guiding device, such as one of resilient guiding devices 60, 60a, 60b and 60c, for example, adapted for one or more of selective linear and nonlinear movement to selectively adjust a height and a position of an eye drop applicator, such as including one or more of vertical, lateral, oblique, and various combinations, paths, and directions of movement, in relation to an eye 110. Also, various embodiments of supporting bases 160, 160a, 160b, 160c and 160d are respectively included in the exemplary embodiments of the eye dropper positioning and guiding apparatuses 300a-300k of FIGS. 3A-3K, as can support embodiments of various resilient guiding devices, such as one of resilient guiding devices 60a, 60b and 60c.

For example, referring to FIGS. 3A, 3B, 3F and 3G, the supporting base 160 is illustrated in conjunction with embodiments of the eye dropper positioning and guiding apparatuses 300a and 300b that include an embodiment of the resilient guiding device 60a, and also in conjunction with embodiments of eye dropper positioning and guiding apparatuses 300f and 300g that include an embodiment of the resilient guiding device 60b.

Figure 3C:
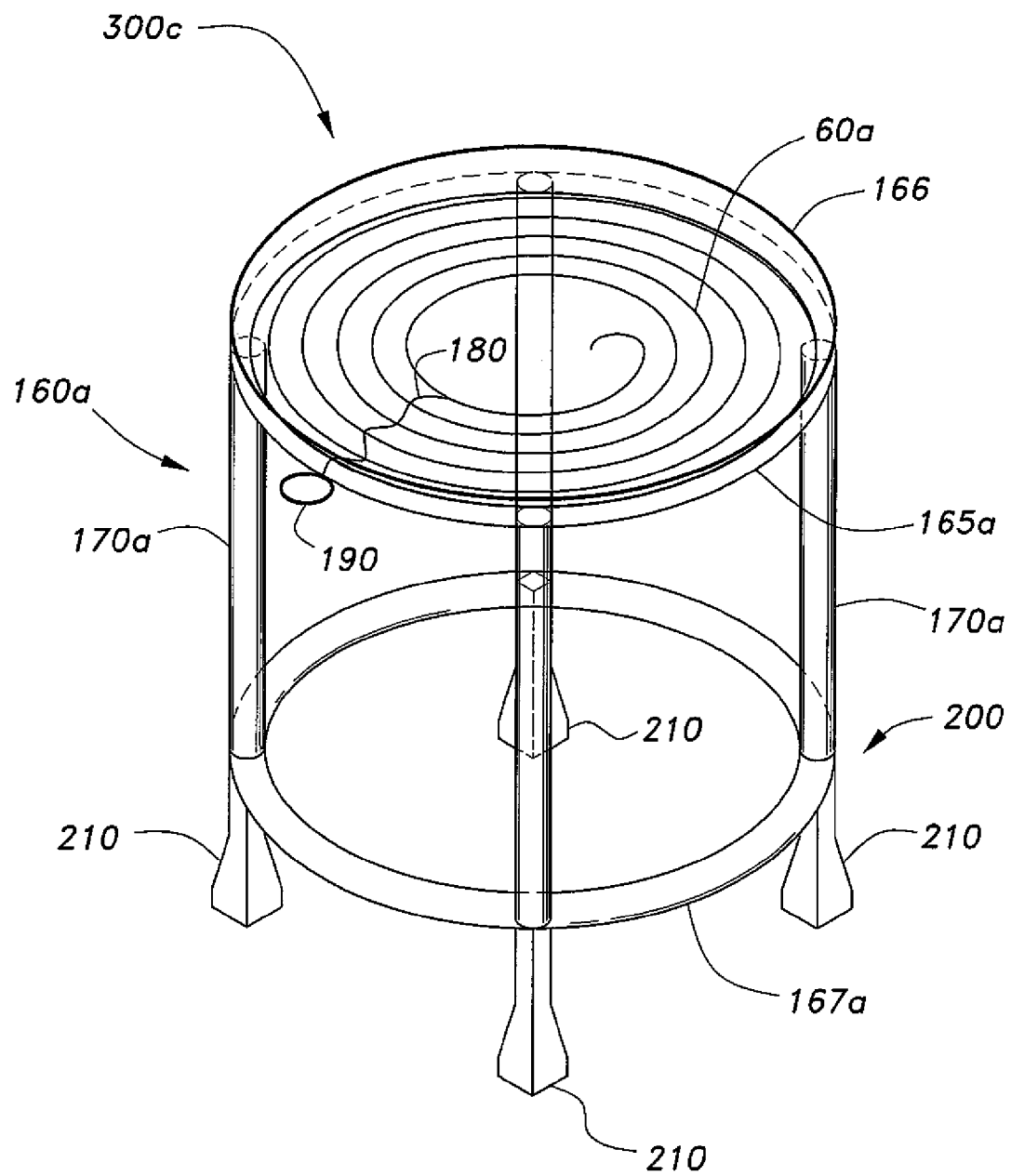
FIG. 3C is an elevated perspective view of an embodiment of an eye dropper positioning and guiding apparatus according to the present invention wherein the supporting base includes support members attached thereto.
Figure 3E:
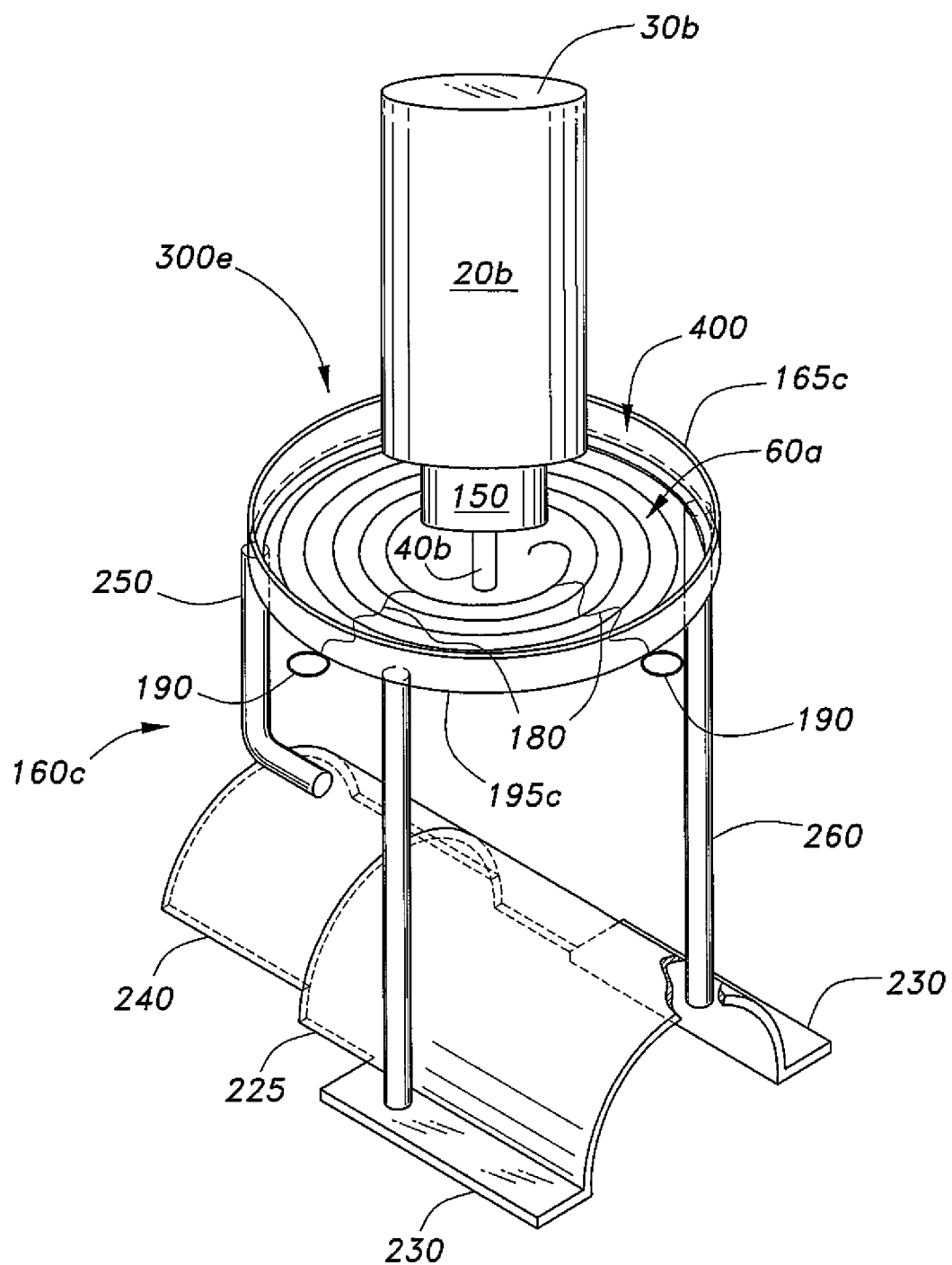
FIG. 3E is an elevated perspective view of an embodiment of an eye dropper positioning and guiding apparatus including a supporting base having a generally saddle type shape according to the present invention.
Figure 3F:
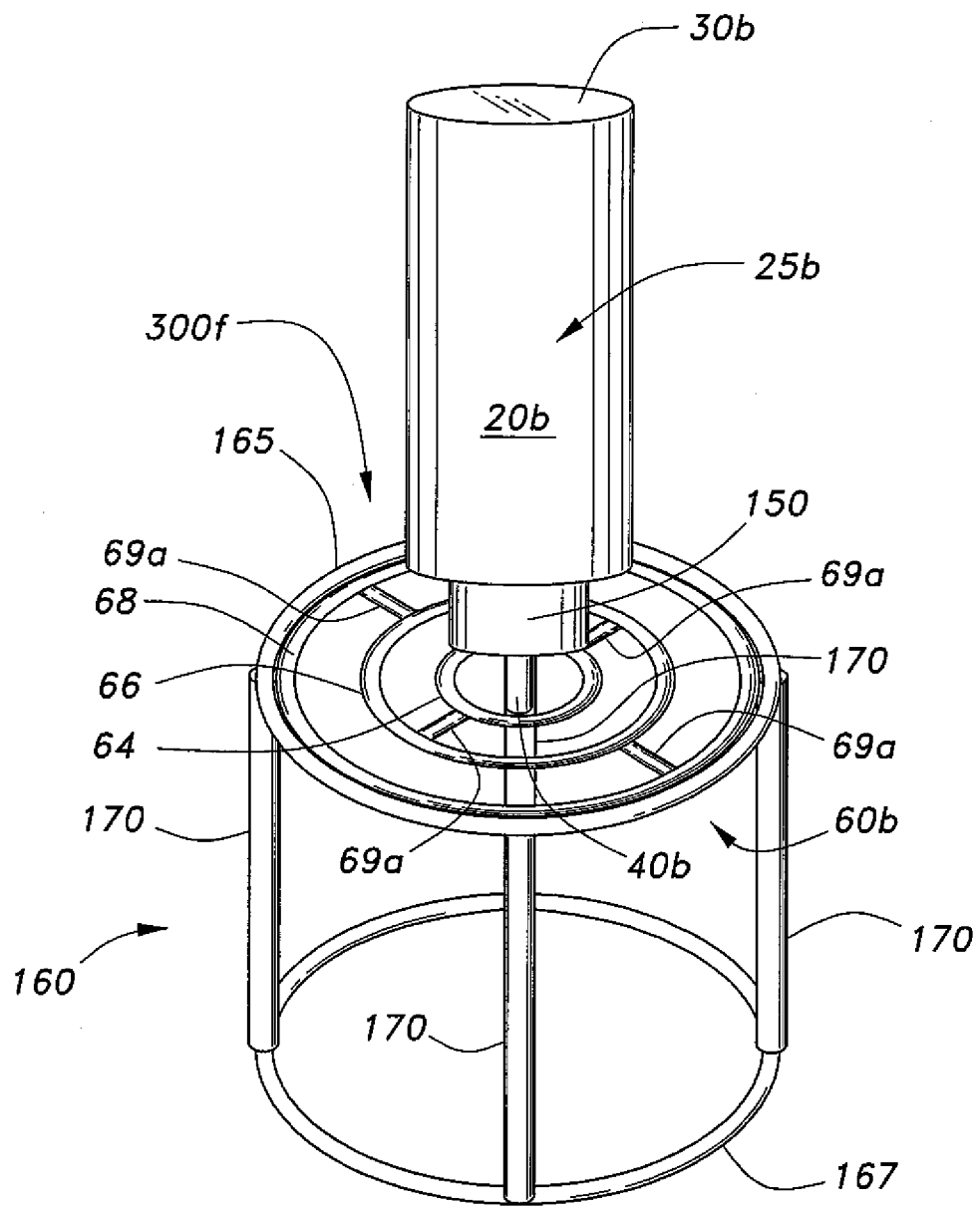
FIG. 3F is an elevated perspective view of an embodiment of an eye dropper positioning and guiding apparatus including a resilient guiding device in a normal state having concentric, interconnected rings according to the present invention.
Figure 3G:
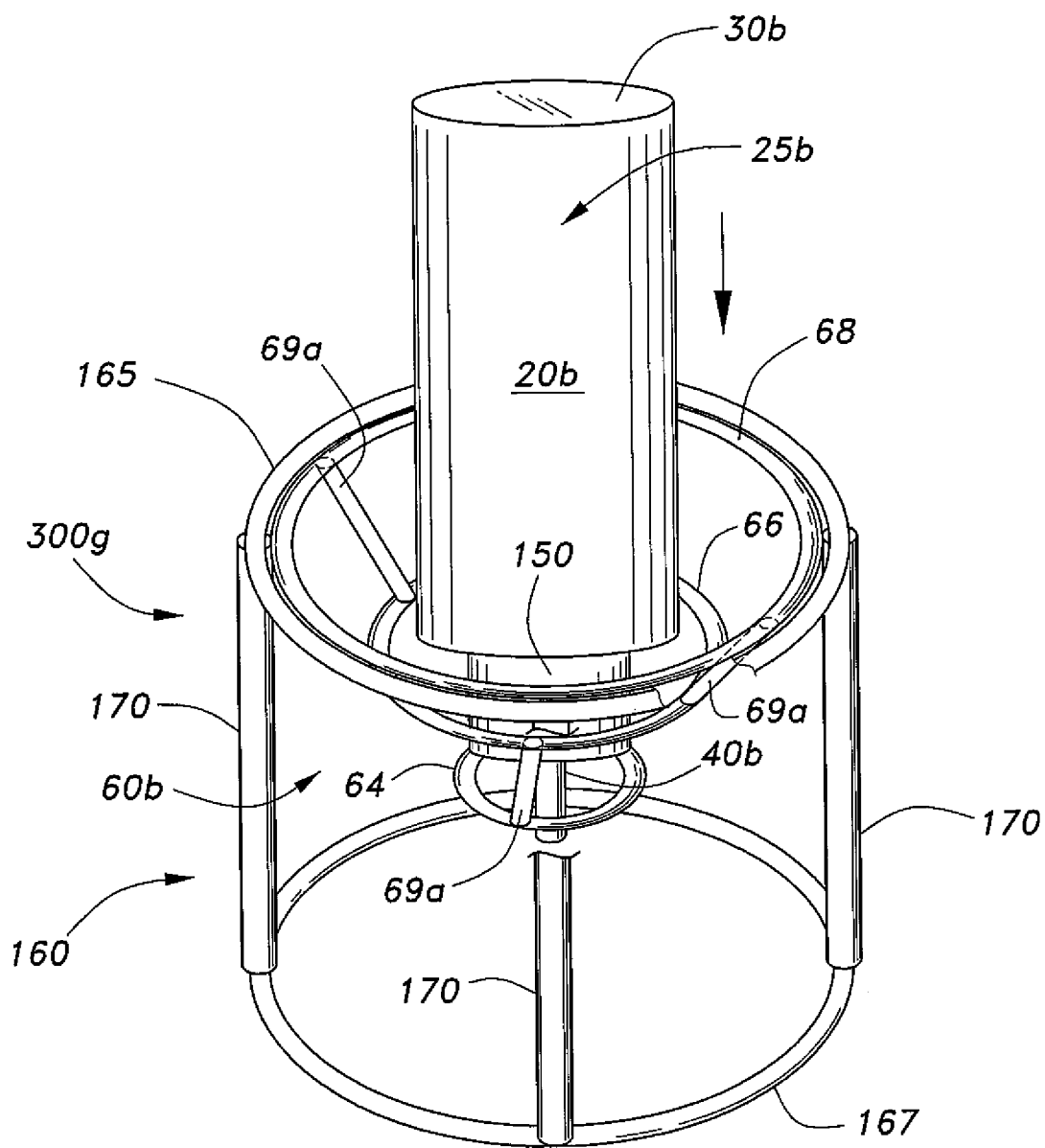
FIG. 3G is an elevated perspective view of an embodiment of an eye dropper positioning and guiding apparatus including an expanded resilient guiding device having concentric, interconnected rings according to the present invention.
Figure 3H:
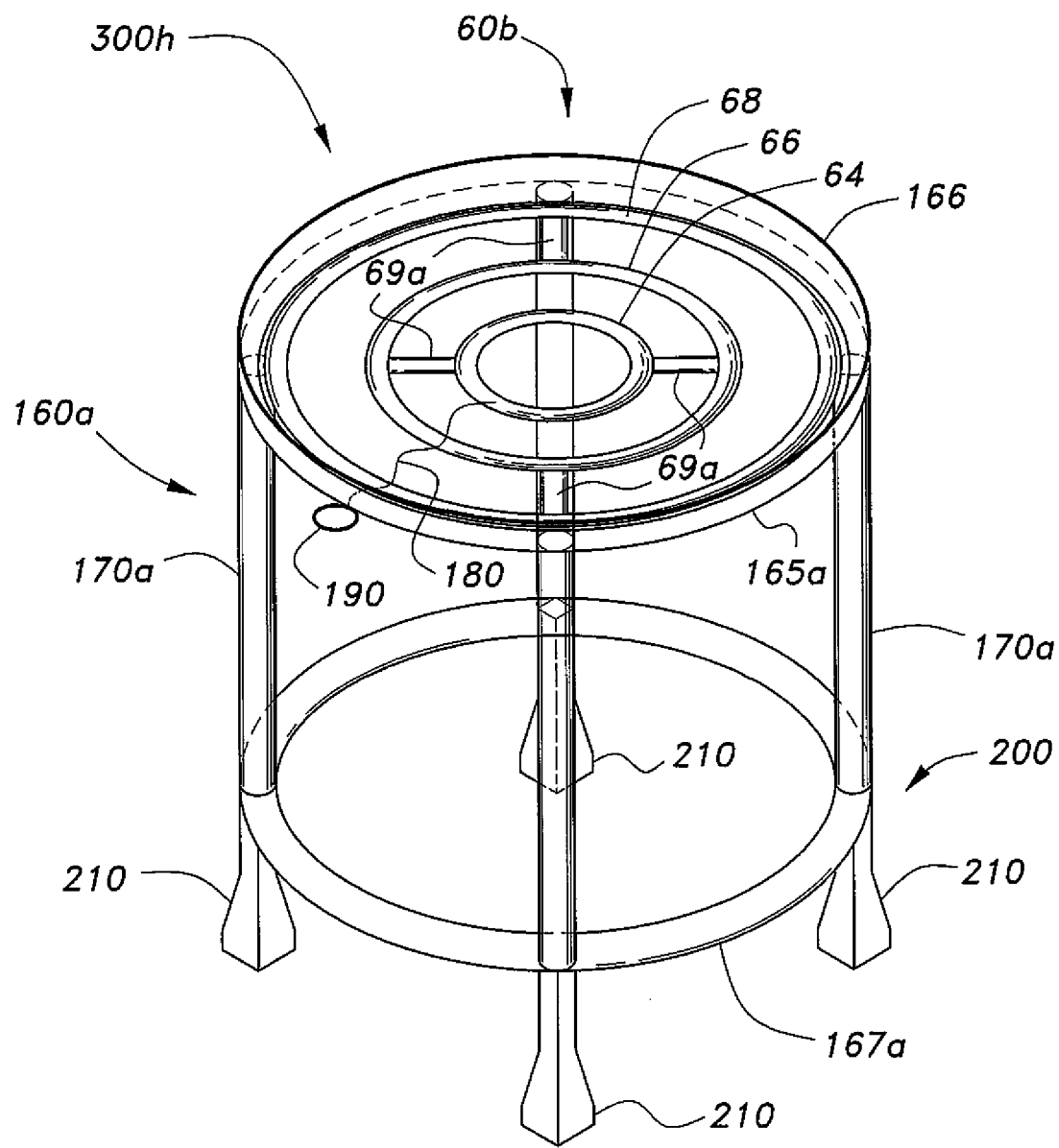
FIG. 3H is an elevated perspective view of an embodiment of an eye dropper positioning and guiding apparatus including a resilient guiding device having concentric, interconnected rings and a supporting base having support members attached thereto according to the present invention.

Also, for example, referring to FIGS. 3C and 3H, the supporting base 160a is illustrated in conjunction with embodiments of the eye dropper positioning and guiding apparatuses 300c, that includes an embodiment of the resilient guiding device 60a, and 300h, that includes an embodiment of the resilient guiding device 60b.

Figure 3I:
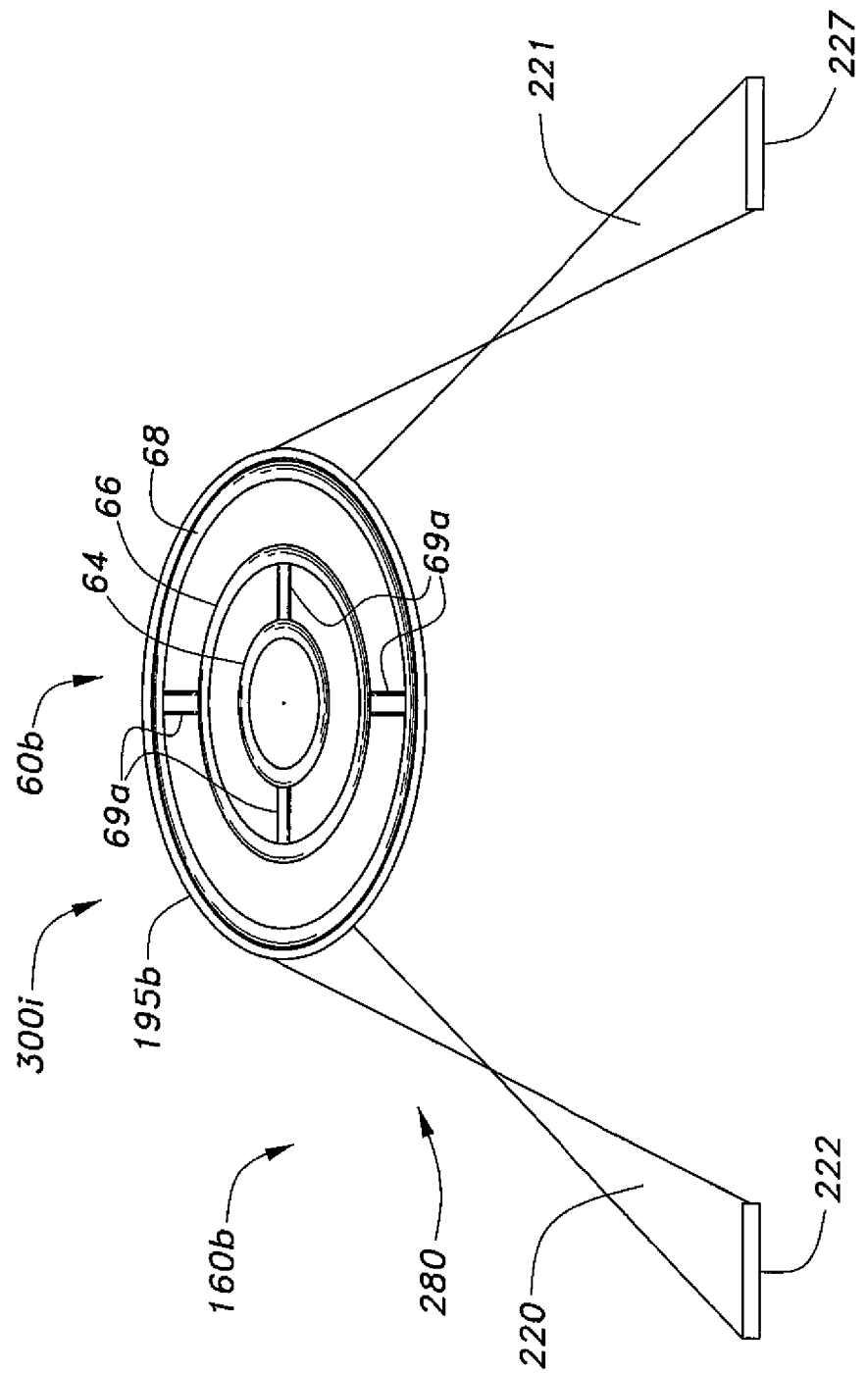
FIG. 3I is an elevated perspective view of an embodiment of an eye dropper positioning and guiding apparatus including a resilient guiding device having concentric, interconnected rings and a supporting base including an eye bridge.

Further, for example, referring to FIGS. 3D and 3I, the supporting base 160b is illustrated in conjunction with embodiments of the eye dropper positioning and guiding apparatuses 300d, that includes an embodiment of the resilient guiding device 60a, and 300i that includes an embodiment of the resilient guiding device 60b.

Figure 3J:
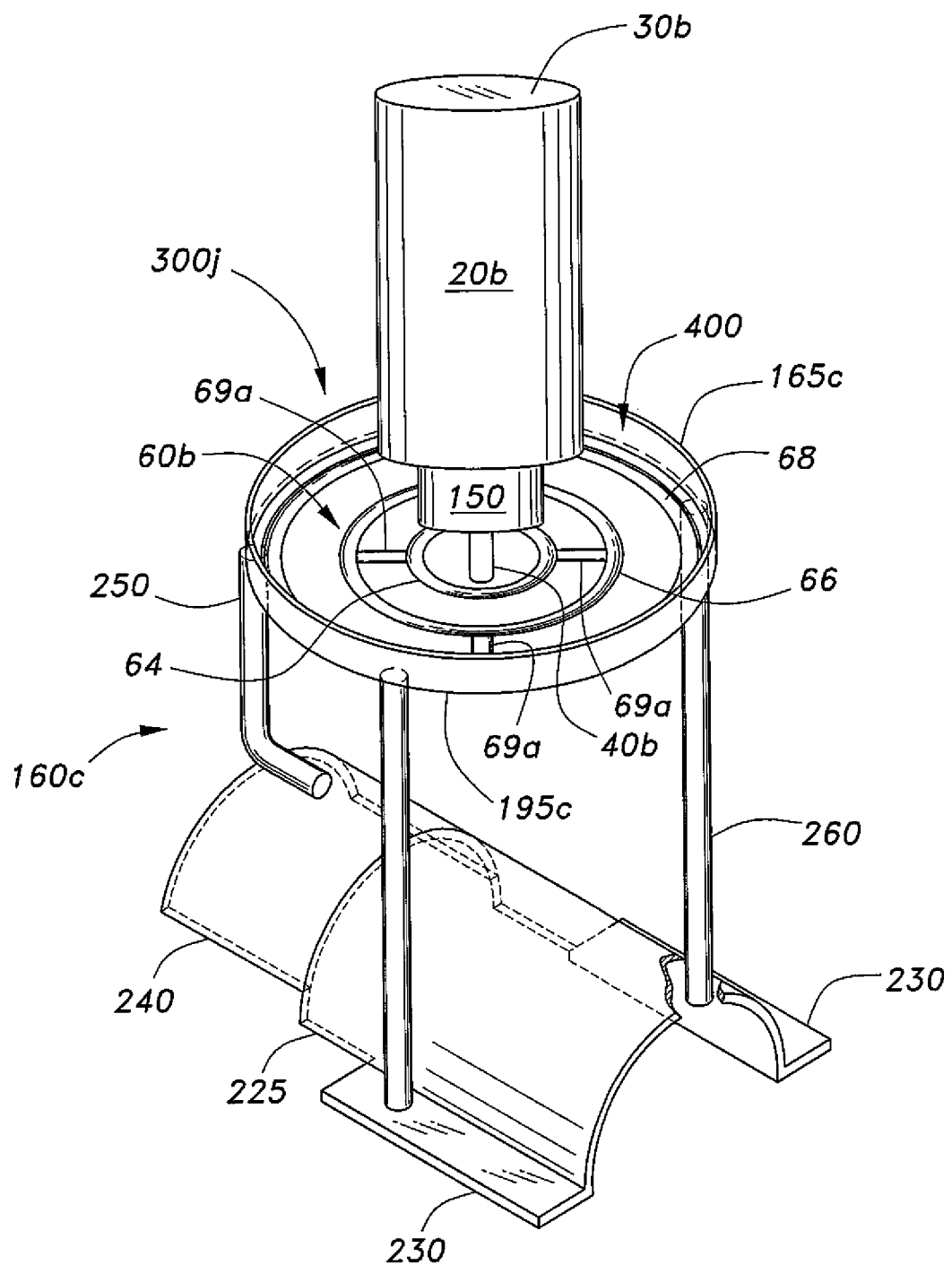
FIG. 3J is an elevated perspective view of an embodiment of an eye dropper positioning and guiding apparatus including a supporting base having a generally saddle type shape and a resilient guiding device including concentric, interconnected rings according to the present invention.

Also, for example, referring to FIGS. 3E and 3J, the supporting base 160c is illustrated in conjunction with embodiments of the eye dropper positioning and guiding apparatuses 300e, that includes an embodiment of the resilient guiding device 60a, and 300j, that includes an embodiment of the resilient guiding device 60b. Additionally, for example, referring to FIG. 3K, the supporting base 160d is illustrated in conjunction with embodiments of the eye dropper positioning and guiding apparatus 300k, that includes an embodiment of the resilient guiding device 60c.

Figure 2A:
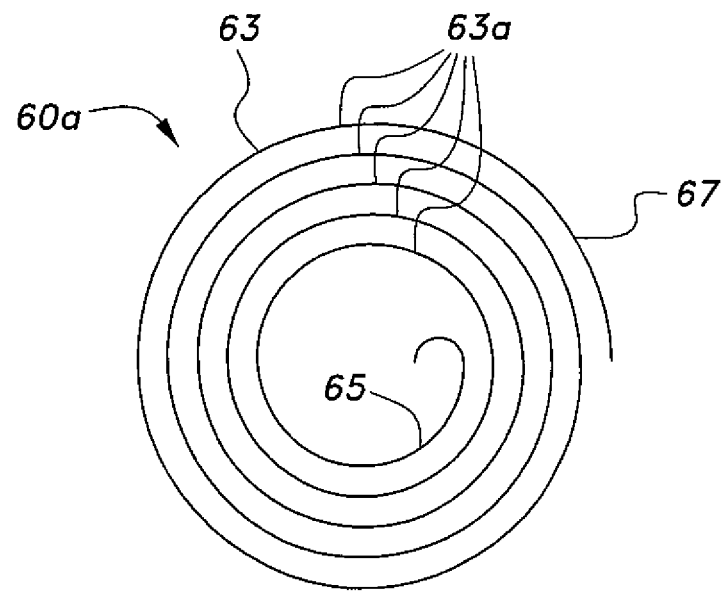
FIG. 2A is an illustration of an embodiment of a resilient guiding device according to the present invention.

Referring now to FIG. 2A, an embodiment of a resilient guiding device 60a is shown that includes and is formed by a selectively expandable member 63, illustrated in FIG. 2A in a normal state. The selectively expandable member 63 includes a plurality of concentric loops 63a, such as of a generally circular configuration, respectively encircling one another from an outermost loop 67 to an innermost loop 65 of the concentric loops 63a, the innermost loop 65 having a first diameter or a first crosswise dimension and the outermost loop 67 having a second diameter or a second crosswise dimension greater than the first diameter or the first crosswise dimension, the innermost loop 65 adapted to receive an eye drop applicator, such as eye drop applicators 20, 20a and 20b.

It is to be noted that the selectively expandable member 63 can be formed from metallic or polymeric material, for example, and should not be construed in a limiting sense. It is to be known that the selectively expandable member 63 is not limited to having a plurality of concentric, generally circular loops but can also include loops having various concentric shapes such as generally rectangular, square, triangular, diamond or elliptical configurations or loops, for example, and should not be construed in a limiting sense. The selectively expandable member 63 can be stretched or expanded by applying a generally vertical force, such as by selectively pushing downward or in a generally downward vertical direction toward the eye 110 and/or can be one or more of selectively linearly and nonlinearly adjusted to selectively adjust a height and a position of an eye drop applicator in relation to the eye 110, such as including one or more of vertical, lateral, oblique, and various combinations, paths, and directions of movement, so that the eye drop(s) fluid can be administered into the eye 110, as illustrated in FIG. 3B, for example. As illustrated in FIG. 3A, a supporting base 160 can be positioned in conjunction with, such as by being set on or coupled to, the resilient guiding device 60a, the supporting base 160 being adapted to position over at least a portion of an area of a face proximate to the eye 110 to support the resilient guiding device 60a. The gaps between the concentric loops 63a provide space for the resilient guiding device 60a to expand, as a selectively expandable member 63, for example.

It is to be noted that the resilient guiding device 60a can be formed from various suitable materials, as can depend on the use or application, such as a material that provides a resilient nature to the device, such as a metal and/or polymeric material, for example, and should not be construed in a limiting sense. The number of concentric loops 63a, including the innermost loop 65 and the outermost loop 67, can range from three to ten, for example, as can depend on the particular use or application, and should not be construed in a limiting sense. It is desirable that the number of concentric loops 63a, including the innermost loop 65 and the outermost loop 67, be between five and six concentric loops 63a, for example. Also, the resilient guiding device 60a can be positioned in conjunction with, such as being set on or coupled to, various embodiments of a supporting base, such as one of supporting bases 160, 160a, 160b, 160c and 160d, as discussed further below with reference to FIGS. 3A-3K, for example, and should not be construed in a limiting sense.

Figure 2B:
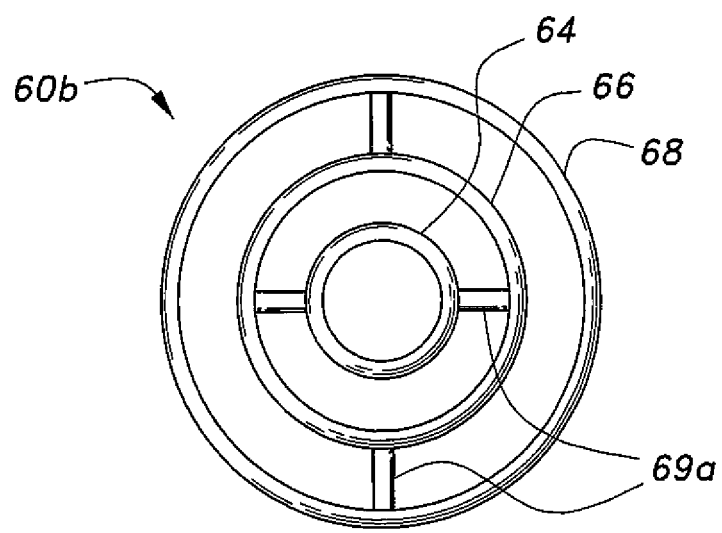
FIG. 2B is an illustration of an embodiment of a resilient guiding device according to the present invention.
Figure 2C:
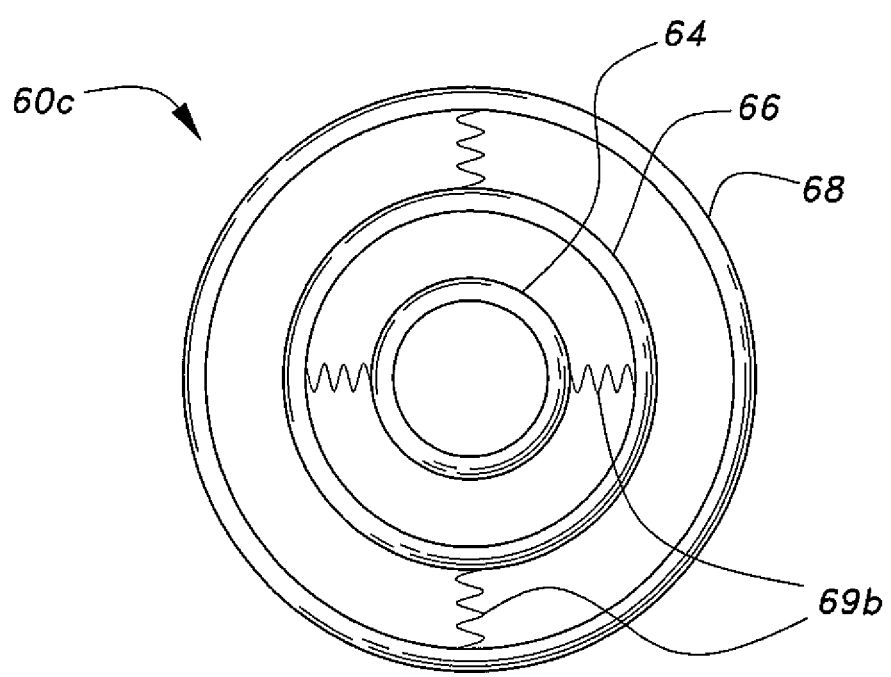
FIG. 2C is an illustration of an embodiment of a resilient guiding device according to the present invention.

As illustrated in FIGS. 2B and 2C, embodiments of resilient guiding devices 60b and 60c are respectively illustrated, each being shown in a normal state, the normal state being a generally planar arrangement, having a plurality of concentric, interconnected generally circular rings, such as concentric, generally circular rings 64, 66 and 68, adapted for one or more of selective linear and nonlinear movement to selectively adjust a height and a position of an eye drop applicator, such as including one or more of vertical, lateral, oblique, and various combinations, paths, and directions of movement, in relation to the eye 110. The innermost concentric, generally circular ring 64 has a first diameter or a first crosswise dimension and the outermost concentric, generally circular ring 68 has a second diameter or a second crosswise dimension greater than the first diameter or the first crosswise dimension. As illustrated in FIGS. 3F and 3G, the resilient guiding device, such as one of resilient guiding devices 60a, 60b and 60c, is positioned in conjunction with, such as being set on or coupled to, the supporting base 160. The supporting base 160 is adapted to be positioned over at least a portion of an area of a face proximate to the eye 110 to support the resilient guiding device 60b, as well as one of resilient guiding devices 60a and 60c, such as positioned over the periorbital region 90 of the eye 110 or in proximity to the eye socket 95 of the eye 110, for example.

Figure 3K:
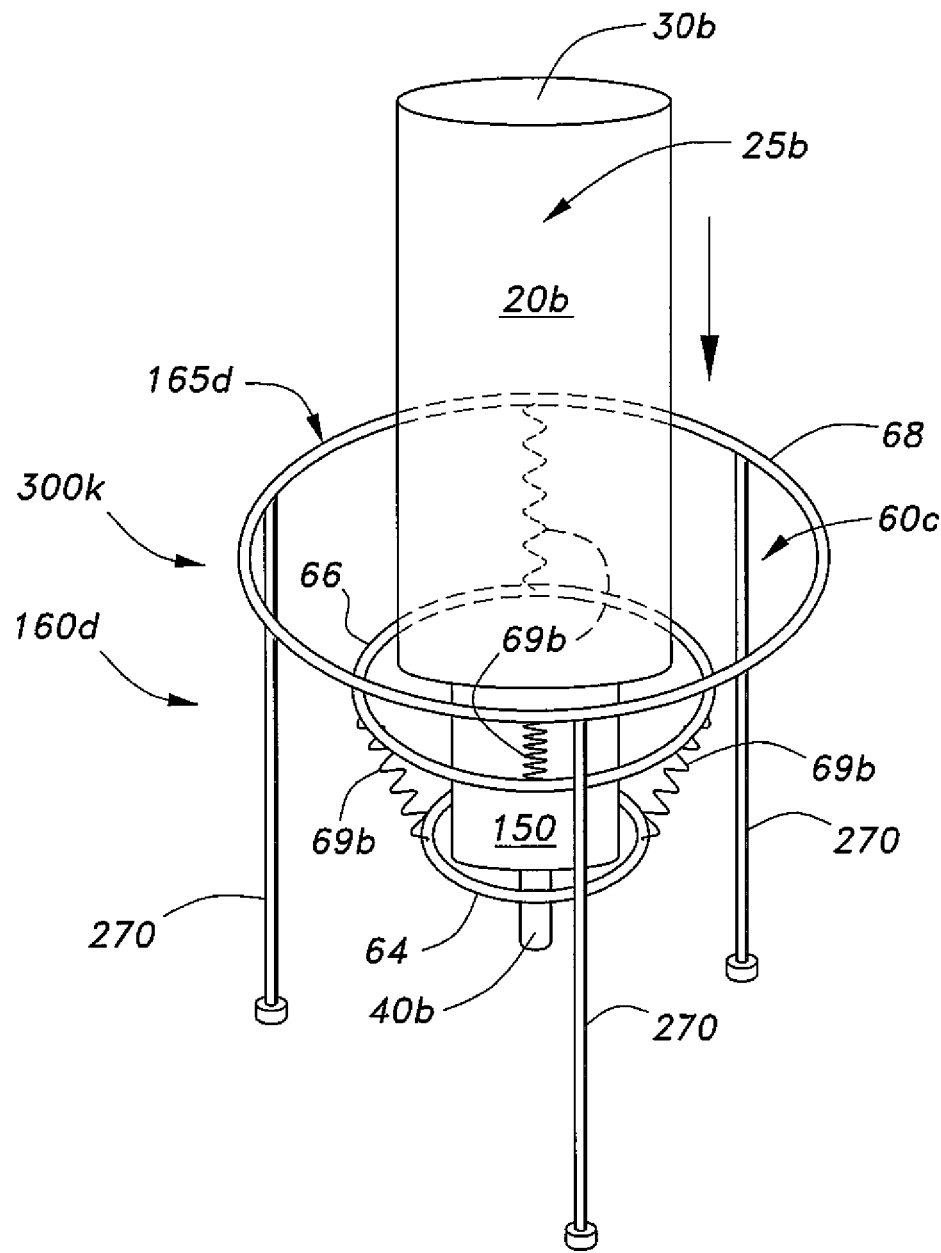
FIG. 3K is an elevated perspective view of an embodiment of an eye dropper positioning and guiding apparatus having a supporting base and an expanded resilient guiding device including concentric, interconnected rings according to the present invention.

Referring also to FIG. 3K, in the embodiment of the eye dropper positioning and guiding apparatus 300k, the supporting base 160d is coupled to or can form a part of the resilient guiding device 60c, as can form or constitute a ring member 165d of the supporting base 160d as can also constitute the outermost ring 68 of the resilient guiding device 60c, for example. The supporting base 160d can also be similarly coupled to or can form a part of one of the resilient guiding devices 60a and 60b, for example, and should not be construed in a limiting sense. The supporting base 160d also includes a plurality of vertical support members 270 adapted to be positioned over the periorbital region 90 of the eye 110 or positioned in proximity to the eye socket 95 of the eye 110 to support the resilient guiding device 60c, for example. It is to be known that the ring member 165d of the supporting base 160d, as can form the outermost ring 68 of the resilient guiding devices 60b and 60c or the outermost loop 67 of the resilient guiding device 60a, is not limited to having a generally circular configuration, but can also include a ring or a loop having various configurations, such as generally rectangular, square, triangular, diamond or elliptical configurations, for example, and should not be construed in a limiting sense.

In embodiments of the resilient guiding devices 60b and 60c, it is to be noted that the concentric, generally circular rings, such as concentric, generally circular rings 64, 66 and 68, as can also include the ring member 165d of FIG. 3K, can be interconnected via resilient members, such as one or more resilient members 69a of resilient guiding device 60b and one or more resilient members 69b of resilient guiding device 60c. The one or more resilient members 69a are of a generally elastic type material construction and the one or more resilient members 69b are of a generally spring-like construction. However, the type and construction of the one or more resilient members 69a and the one or more resilient members 69b can be of various suitable materials and constructions, and should not be construed in a limiting sense. Various suitable resilient materials for the resilient members 69a and 69b can include a suitable elastomeric material, such as a stretchable polymeric material, elastic rubber or metal or plastic stretchable springs, for example, that can assist in controlling the one or more of selective linear and nonlinear movement to selectively adjust a height and a position of the eye drop applicator in relation to the eye 110, as illustrated in FIGS. 3F, 3G, 3J and 3K, such as of eye drop applicators 20, 20a and 20b, for example.

Further, the number of concentric, generally circular rings, such as concentric, generally circular rings 64, 66 and 68, can vary between two to four, for example, in the resilient guiding devices 60*b* and 60*c*. It is desirable, however, to have between two or three concentric, generally circular rings, such as concentric, generally circular rings 64, 66 and 68, forming the innermost ring 64, the middle ring 66, and the outermost ring 68. It is to be known that the resilient guiding devices 60*b* and 60*c*, respectively, are not limited to having a plurality of concentric, generally circular rings but can also include various other concentric shapes such as generally rectangular, square, triangular, diamond or elliptical configurations or rings, for example, and should not be construed in a limiting sense.

The concentric generally circular rings, such as concentric, generally circular rings 64, 66 and 68, when in the normal state, can be arranged in a generally planar arrangement, having the innermost ring 64 having the smallest diameter or smallest crosswise dimension in the inside of the arrangement and the outermost ring 68 having the largest diameter or the largest crosswise dimension on the outside of the arrangement. It is to be noted that the concentric, generally circular rings, such as concentric, generally circular rings 64, 66 and 68, when in an expanded state, can also be arranged by having one ring above another according to their size. For example, the ring with the smallest diameter or the smallest crosswise dimension can be on the bottom of the arrangement and the ring with the largest diameter or largest crosswise dimension can be on the top of the arrangement, as illustrated in FIGS. 3G and 3K, for example, as for the concentric, interconnected generally circular rings, such as concentric, generally circular rings 64, 66 and 68 of the resilient guiding devices 60*b* and 60*c*. Also, the resilient guiding devices 60*b* and 60*c*, as well as the resilient guiding device 60*a*, can be respectively positioned in conjunction with, such as being set on or coupled to, various embodiments of a supporting base, such as supporting bases 160, 160*a*, 160*b*, 160*c* and 160*d*, as discussed further below with reference to FIGS. 3A-3K, for example, and should not be construed in a limiting sense.

Referring now to FIGS. 3A and 3F, the resilient guiding device, such as one of resilient guiding devices 60*a*, 60*b* and 60*c*, can be adapted to receive various types of eye drop applicators, such as one of eye drop applicators 20, 20*a* and 20*b*, as can be conventional, specialized or non-conventional eye drop applicators, used to administer the medicated and non-medicated eye fluid into the eye 110 (FIG. 1A). It is to be noted that the resilient guiding device, such as resilient guiding device 60*a* in FIG. 3A, can include at least one safety lock 190 associated with a corresponding at least one connecting member 180, the at least one connecting member 180 connecting at least the innermost loop 65 and one or more loops 63*a*, as can also include the outermost loop 67, of the resilient guiding device 60*a*. The safety lock 190 and the associated connecting member 180 can be formed from various suitable materials, such as a metallic wire type material, a metallic chain type material, a thread type material, or a combination thereof, for example, to assist in preventing overstretching of the resilient guiding device, such as resilient guiding device 60*a*, for example.

Also, it is to be noted that embodiments of a resilient guiding device, such as one of resilient guiding devices 60*a*, 60*b* and 60*c*, can similarly include the at least one safety lock 190 associated with a corresponding at least one connecting member 180 in communicating relation with the innermost ring 64 or with the innermost loop 65, respectively, as well as being in communicating relation with a corresponding one of supporting bases 160*a*, 160*b*, 160*c* and 160*d* and/or in communicating relation with the outermost ring 68 or with the outermost loop 67, respectively, as illustrated in FIGS. 3A, 3B and 3H, for example. As further illustrated in FIGS. 3B and 3H, the connecting member 180 is adapted to limit one or more of the selective linear and nonlinear movement to a predetermined range of movement in selectively adjusting a height and a position of an eye drop applicator in relation to the eye 110, such as including one or more of vertical, lateral, oblique, and various combinations, paths, and directions of movement, of at least the innermost ring 64 or the innermost loop 65 and at least one middle ring 66 or a middle loop 63*a* of the resilient guiding device, such as one of resilient guiding devices 60*a*, 60*b* and 60*c*, for example.

Further, it is to be noted that the connecting member 180 associated with the safety lock 190 can connect the innermost ring 64 (FIG. 3H) or the innermost loop 65 (FIG. 3A) of the resilient guiding device, such as one of resilient guiding devices 60*a*, 60*b* and 60*c*, to either the first ring member 165 or 165*a*, or the ring member 165*d*, of the supporting base, such as one of corresponding supporting bases 160, 160*a*, and 160*d*, or a holder 195*c* of supporting base 160*c*, or the holder 195*b* of the supporting base 160*b*. The connecting member 180 associated with the safety lock 190 can also be in communication with one or more of the other loops 63*a* or with one or more of the other rings, such as rings 66 and 68, for example, of the corresponding resilient guiding device 60*a*, 60*b* or 60*c*, for example.

The at least one safety lock 190 and at least one associated connecting member 180 can limit or restrict the overstretching of resilient guiding device, such as one of the resilient guiding devices 60*a*, 60*b* and 60*c*, and can assist in preventing possible damage as can be caused by direct contact between the nozzle, such as one of nozzles 40, 40*a* and 40*b*, and the eye 110 (FIG. 1A). The length of the connecting member 180 associated with the safety lock 190 can be pre-adjusted, such as in length, arrangement or position, before using the safety lock 190 and the connecting member 180 in conjunction with embodiments of eye dropper positioning and guiding apparatuses, such as with the eye dropper positioning and guiding apparatuses 300*a*-300*k*, for example.

Continuing with reference to FIGS. 3A, 3B, 3F and 3G, the supporting base 160 includes the first ring member 165 and the resilient guiding device, such as one of resilient guiding devices 60*a*, 60*b* and 60*c*, is positioned in conjunction with, such as being set on or coupled to, the first ring member 165. The supporting base 160 also includes a second ring member 167 adapted to be positioned over a periorbital region of an eye 110 (FIG. 1A) or placed in proximity to the eye socket 95 of the eye 110, depending on the diameter or the crosswise dimension of the second ring member 167, and includes a plurality, desirably four, connecting members 170 connecting the first ring member 165 and the second ring member 167. The outermost loop 67 of the resilient guiding device 60*a* or the outermost ring 68 of the resilient guiding device 60*b* or 60*c* can be positioned in conjunction with, such as being set on or coupled to, the first ring member 165 of the supporting base 160. The second ring member 167 of FIGS. 3A, 3B, 3F and 3G can be adapted to be positioned over the periorbital region 90 (FIG. 1A) of the eye 110 (FIG. 1A) or positioned in proximity to the eye socket 95, as can assist in preventing or limiting the eye lids from blinking or closing before or as the medication enters the eye 110 (FIG. 1A), or in proximity to the eye socket 95 of the eye 110. It is to be known that the first ring member 165 and the second ring member 167 are not limited to having a generally circular configuration, but can also include ring members having various configurations, such as generally rectangular, square, triangular, diamond or elliptical configurations, for example, and should not be construed in a limiting sense.

Also, referring now to FIGS. 3A, 3B, 3F and 3G, during or before use, when the person administering the eye medication pushes or moves the base 30 or 30*b* or the bulb 120 of the eye drop applicator, such as one of eye drop applicators 20, 20*a* and 20*b*, when positioned in the resilient guiding device, such as one of resilient guiding devices 60*a*, 60*b* and 60*c*, the eye drop applicator can be one or more of selectively linearly and nonlinearly moved to selectively adjust a height and a position of the eye drop applicator in relation to the eye 110 to adjust the nozzle, such as one of nozzles 40, 40*a* and 40*b*. Likewise, the resilient guiding device, such as one of resilient guiding devices 60*a*, 60*b*, and 60*c*, can be adjusted one or more of selectively linearly and nonlinearly to selectively adjust a height and a position of the eye drop applicator in relation to the eye 110, when positioned in the resilient guiding device, such as one of resilient guiding devices 60*a*, 60*b* and 60*c*, such as including one or more of vertical, lateral, oblique, and various combinations, paths, and directions of movement, as can allow the nozzle, such as nozzle 40*b*, of the eye drop applicator, such as eye drop applicator 20*b*, to be aligned properly so as to get as close to, or at an acceptable position and distance from, the eye 110 (FIG. 1A) to administer the eye drop(s) fluid. After administering the eye drop(s) fluid, the resilient guiding device, such as one of resilient guiding devices 60*a*, 60*b* and 60*c*, can then return to, as well as the eye drop applicator therein, such as eye drop applicator 20*b*, to an original position after subsequent release of pressure thereon that adjusted the position of the eye drop applicator, as described herein, to administer the eye drop(s) fluid. It is to be appreciated that the resilient guiding devices, such as resilient guiding devices 60, 60*a*, 60*b*, and 60*c* can be compressible, stretchable or expandable, and resilient in nature, for example.

Referring to FIGS. 3C and 3H, embodiments of the eye dropper positioning and guiding apparatuses 300*c* and 300*h* are substantially similar to the embodiments of the eye dropper positioning and guiding apparatuses 300*a*, 300*b*, 300*f* and 300*g* described in relation to FIGS. 3A, 3B, 3F and 3G. Similar to the embodiments described in FIGS. 3A, 3B, 3F and 3G, the embodiments of the supporting base 160*a* in FIGS. 3C and 3H includes the first ring member 165*a* having a first diameter or a first crosswise dimension. The resilient guiding device, such as one of resilient guiding devices 60*a*, 60*b* and 60*c* can be positioned in conjunction with, such as being set on or coupled to, the first ring member 165*a*. The supporting base 160*a* in FIGS. 3C and 3H also includes a second ring member 167*a* adapted to be positioned in proximity to the eye socket 95 of the eye 110. Also, similarly, the supporting base 160*a* in FIGS. 3C and 3H includes a plurality, desirably four, connecting members 170*a* connecting the first ring member 165*a* and the second ring member 167*a*.

A difference between the embodiments described in FIGS. 3A, 3B, 3F and 3G and those in FIGS. 3C and 3H, however, is that the second ring member 167*a* of the supporting base 160*a* in FIGS. 3C and 3H is associated with a vertical extension member 200, as described. The vertical extension member 200 includes a plurality, desirably four, support members 210, and can be of a fixed length or adjustable in length, for example. The support members 210 are coupled to the second ring member 167*a* to position the supporting base 160*a* over at least a portion of the area of a face proximate to the eye 110, such as in proximity to the eye socket 95 of the eye 110, with the second ring member 167*a* desirably being positioned in spaced relation to the portion of the area of a face proximate to the eye 110. It is to be noted that the vertical extension member 200 with the support members 210 can allow for an adjustment in height of the supporting base 160*a* as can assist in accommodating or allowing eye drop applicators having unconventionally or relatively long nozzles, for example. The opening in the middle of the second ring member 167*a* coupled to the plurality of support members 210 can allow the support members 210 to be adapted to fit over the periorbital region 90 (FIG. 1A) of the eye 110 (FIG. 1A) or positioned in proximity to the eye socket 95, as can assist in preventing or limiting the eye lids from blinking or closing before or as the medication fluid enters the eye 110 (FIG. 1A), or in proximity to the eye socket 95 of the eye 110, for example.

A further difference between the embodiments described in FIGS. 3A, 3B, 3F and 3G and those in FIGS. 3C and 3H is that the first ring member 165*a* of the supporting base 160*a* can be adapted to include an upward extension sleeve 166 as in FIGS. 3C and 3H, to hold and support the resilient guiding device, such as one of resilient guiding devices 60*a*, 60*b* and 60*c*. It is to be noted that the upward extension sleeve 166 can also be adapted to be included with other embodiments of the supporting bases 160, 160*a*, 160*b*, 160*c* and 160*d*, for example, and should not be construed in a limiting sense. It is to be known that the first ring member 165*a* and the second ring member 167*a* are not limited to having a generally circular configuration, but can also include ring members having various configurations, such as generally rectangular, square, triangular, diamond or elliptical configurations, for example, and should not be construed in a limiting sense.

Referring now to FIGS. 3D and 3I, embodiments of the eye dropper positioning and guiding apparatuses 300*d* and 300*i* are illustrated. A difference between the embodiments described in FIGS. 3A, 3B, 3F and 3G and the embodiments 300*d* and 300*i* described in FIGS. 3D and 3I is that the supporting base 160*b* in FIGS. 3D and 3I includes an eye bridge 280 including a holder 195*b*, as can include an upward extension sleeve, similar to the upward extension sleeve 166, to hold and support one of the resilient guiding devices 60*a*, 60*b* and 60*c* in the holder 195*b*. The holder 195*b* is coupled for support to a first lateral support member 220 and a second lateral support member 221. The resilient guiding device, such as one of the resilient guiding devices 60*a*, 60*b* and 60*c*, can be positioned in conjunction with, such as being set on or coupled to, the holder 195*b*.

The first lateral support member 220 and the second lateral support member 221 can be erected in a vertical or substantially vertical position, wherein the resilient guiding device, such as one of resilient guiding devices 60*a*, 60*b* and 60*c*, is positioned in conjunction with, such as being set on or coupled to, the holder 195*b* and supported by the first lateral support member 220 and the second lateral support member 221. An end 222 of the first lateral support member 220 and an end 227 of the second lateral support member 221 typically are located at a position furthest from the holder 195*b* and can be adapted to include pads that can protect a region about the eye 110 (FIG. 1A) or can protect a portion of an area of a face proximate to the eye on which the ends 222 and 227 rest to support the supporting base 160*b*, such as when the end 222 of the first lateral support member 220 and the end 227 of the second lateral support member 221 are placed in proximity to the eye socket 95 of the eye 110. It is to be known that the holder 195b is not limited to having a generally circular configuration, but can also include holders having various configurations, such as generally rectangular, square, triangular, diamond or elliptical configurations, for example, and should not be construed in a limiting sense.

By way of operation, to support the holder 195b having the resilient guiding device, such as one of resilient guiding devices 60a, 60b and 60c, over the eye 110 (FIG. 1A), the first lateral support member 220 is typically placed on the person's forehead and the second lateral support member 221 is typically placed on the maxillary region of the face, for example. Once the resilient guiding device, such as one of resilient guiding devices 60a, 60b and 60c, has been positioned over the eye 110 (FIG. 1A), such as by adjusting or positioning the first and second lateral support members 220 and 221, the eye drop applicator can be inserted into the resilient guiding device, such as one of resilient guiding devices 60a, 60b and 60c, where it can be selectively adjusted one or more of linearly and nonlinearly to selectively adjust a height and a position of the eye drop applicator in relation to the eye 110, such as including one or more of vertical, lateral, oblique, and various combinations, paths, and directions of movement, to assist in properly administering the eye drop(s) fluid into the eye 110 (FIG. 1A).

Referring now to FIGS. 3E and 3J, embodiments of the eye dropper positioning and guiding apparatuses 300e and 300j are illustrated. A difference between the embodiments described in FIGS. 3A, 3B, 3F and 3G and the embodiments of the eye dropper positioning and guiding apparatuses 300e and 300j described in FIGS. 3E and 3J is that the supporting base 160c in FIGS. 3E and 3J includes a body 225 having a generally saddle type shape adapted to position over at least a portion of a nose in an area that is in proximity to the eye 110. The supporting base 160c includes the holder 195c adapted to support the resilient guiding device, such as one of resilient guiding devices 60a, 60b and 60c. The resilient guiding device, such as one of resilient guiding devices 60a, 60b and 60c, can be positioned in conjunction with, such as being set on or coupled to, the holder 195c.

The holder 195c can also be associated with an upward extension sleeve 165c, similar to the upward extension sleeve 166 of FIGS. 3C and 3H, as described. The holder 195c has an inner opening 400 adapted to receive the resilient guiding device, such as one of resilient guiding device 60a, 60b and 60c. The supporting base 160c also includes at least two laterally opposed support members 230 coupled to and extending from the body 225, at least two connecting members 260 respectively connecting the at least two laterally opposed support members 230 to the holder 195c; and a head member 250 connected to the holder 195c and extending from the holder 195c downward to support the holder 195c.

The body 225 is adapted to rest towards the nostrils of the nose and can cover at least a portion of the nose from the top of the nose, as well as a portion of the sides of the nose. The body 225 can be adapted to include a neck, such as a neck 240, to cover the relatively hard portion of the nose closer towards the forehead of the person. It is to be noted that while the shape of the holder 195c can vary, it is desirable that the holder 195c be circular or generally circular in shape or configuration, for example, although other of various suitable shapes or configurations for the holder 195c can be used, such as a generally rectangular, square, triangular, elliptical or diamond shape or configuration, for example, and should not be construed in a limiting sense. The at least two lateral opposed support members 230 are adapted to rest on the maxillary region of the face and on both sides of the nose, for example. The resilient guiding device, such as one of resilient guiding device 60a, 60b and 60c, associated with the inner opening 400 and the holder 195c can allow for the one or more of selective linear and nonlinear movement to selectively adjust a height and a position of the eye drop applicator in relation to the eye 110, such as including one or more of vertical, lateral, oblique, and various combinations, paths, and directions of movement.

It is to be noted that regardless of which supporting base, such as one of supporting bases 160, 160a, 160b, 160c, and 160d, and regardless of which resilient guiding device, such as one of resilient guiding devices 60, 60a, 60b, and 60c, is used, the embodiments of the eye dropper positioning and guiding apparatuses 300a-300k can operate in a similar fashion, for example. It is to be noted that the supporting base and the various components thereof, as described, can be formed from various suitable materials, such as a suitable metallic or plastic type material, or combinations thereof, for example, as can depend on the use or application, and should not be construed in a limiting sense.

By way of operation, the eye drop applicator, such as one of eye drop applicators 20, 20a and 20b, is inserted into the resilient guiding device, such as one of resilient guiding devices 60, 60a, 60b and 60c. If however, the eye drop applicator contains a non-conventional or specialized nozzle, an appropriate attachment member, such as one of attachment members 50 and 50a, can be used to assist in ensuring a proper fit between the nozzle of the eye drop applicator and the resilient guiding device, such as one of resilient guiding devices 60, 60a, 60b and 60c.

Also, prior to the embodiments of the eye dropper positioning and guiding apparatuses 300a-300k being positioned in relation to the periorbital region 90 or in proximity to the eye 110, when included, the at least one connecting member 180 associated with the at least one corresponding safety lock 190 can be adjusted according to the position of the eye 110, as described herein, for example. After the connecting member 180 associated with the corresponding safety lock 190 has been adjusted, the head of the person who is receiving the eye drop(s) fluid is typically reclined backward and the eye dropper positioning and guiding apparatus having the eye drop applicator is positioned over the periorbital region 90 or in proximity to the eye 110, for example. A portion of the supporting base can be positioned over the upper eye lid and a portion of the supporting base can be positioned below the lower eye lid to assist in keeping the eye lids from preventing or limiting the eye drop fluid from reaching the eye 110, for example.

The person who is receiving the eye drop(s) can then look directly toward the nozzle of the eye drop applicator passing through the resilient guiding device, such as one of resilient guiding devices 60, 60a, 60b and 60c. If, however, the person who is receiving the eye drop(s) fluid has a deeply sunken eye ball, the nozzle of the eye drop applicator can be pushed downwards towards the eye by placing pressure on the eye drop applicator and pushing the nozzle of the eye drop applicator toward the eye ball. Once the eye drop applicator is properly aligned or positioned with the eye, the eye drop(s) fluid is administered into the eye by laterally compressing the resilient body, such as one of resilient bodies 25 or 25b or the bulb, such as the bulb 120, of the eye drop applicator, for example. After the eye drop(s) fluid has been administered into the eye, the pressure is released from the eye drop applicator, the resilient, spring-like characteristics of the resilient guiding device, such as one of resilient guiding device 60, 60a, 60b and 60c, can assist in causing the eye drop applicator to move away from the eye 110 (FIG. 1A) so that the likelihood of the nozzle of the eye drop applicator coming into contact with the corneal area of the eye is substantially reduced.

It is to be understood that the present invention is not limited to the embodiments described above, but encompasses any and all embodiments within the scope of the following claims.

We claim:

1. An eye dropper positioning and guiding apparatus, comprising:
   a resilient guiding device adapted for one or more of selective linear and nonlinear movement to selectively adjust a height and a position of an eye drop applicator in relation to an eye including a selectively expandable member having a plurality of concentric loops having an outermost loop and an innermost loop, the innermost loop having an opening adapted to receive the eye drop applicator; and
   a supporting base positioned in conjunction with the resilient guiding device to support the resilient guiding device, the supporting base being adapted to be positioned over at least a portion of an area of a face proximate to the eye, wherein the supporting base comprises:
   i) a body having a generally saddle type shape adapted to be positioned over at least a portion of a nose in the area of the face proximate to the eye;
   ii) a holder coupled to the body, the holder adapted to support the resilient guiding device, the holder having an inner opening adapted to receive the resilient guiding device;
   iii) at least two laterally opposed support members coupled to and extending from the body;
   iv) at least two connecting members respectively connecting the at least two laterally opposed support members to the holder; and
   v) a head member connected to the holder and extending downward from the holder to support the holder.

2. The eye dropper positioning and guiding apparatus according to claim 1, further comprising:
   at least one safety lock comprising at least one connecting member, the at least one connecting member being connected to one or more loops including the innermost loop of the resilient guiding device.

3. An eye dropper positioning and guiding apparatus, comprising:
   a resilient guiding device including a plurality of concentric, interconnected rings adapted for one or more of selective linear and nonlinear movement to selectively adjust a height and a position of an eye drop applicator in relation to an eye including an innermost ring having an opening adapted to receive the eye drop applicator and an outermost ring; and
   a supporting base positioned in conjunction with the resilient guiding device to support the resilient guiding device, the supporting base being adapted to be positioned over at least a portion of an area of a face proximate to the eye, wherein the supporting base comprises:
   i) a body having a generally saddle type shape adapted to be positioned over at least a portion of a nose in the area of the face proximate to the eye;
   ii) a holder coupled to the body, the holder adapted to support the resilient guiding device, and the holder having an inner opening adapted to receive the resilient guiding device;
   iii) at least two laterally opposed support members coupled to and extending from the body;
   iv) at least two connecting members respectively connecting the at least two laterally opposed support members to the holder; and
   v) a head member connected to the holder and extending downward from the holder to support the holder.

4. The eye dropper positioning and guiding apparatus according to claim 3, wherein the resilient guiding device further comprises:
   one or more resilient members respectively connecting the innermost ring and at least one other ring of the plurality of concentric, interconnected rings,
   wherein the one or more resilient members are adapted for one or more of the selective linear and nonlinear movement of the resilient guiding device to selectively position the resilient guiding device in corresponding relation to a portion of the eye.

5. The eye dropper positioning and guiding apparatus according to claim 3, further comprising:
   at least one safety lock comprising at least one connecting member, the at least one connecting member being connected to one or more rings including the innermost ring of the resilient guiding device.

* * * * *